United States Patent
Brunnett et al.

(10) Patent No.: US 9,084,551 B2
(45) Date of Patent: Jul. 21, 2015

(54) METHOD AND SYSTEM FOR MONITORING A NERVE

(75) Inventors: William C. Brunnett, Jacksonville, FL (US); David C. Hacker, Jacksonville, FL (US); John A. Meyer, Hilton Head Island, SC (US); Kevin Lee McFarlin, Jacksonville, FL (US); John Murdock Murphy, St. Johns, FL (US); Dwayne S. Yamasaki, St. Augustine, FL (US); John N. Gardi, San Francisco, CA (US)

(73) Assignee: Medtronic Xomed, Inc., Jacksonville, FL (US)

( * ) Notice: Subject to any disclaimer, the term of this patent is extended or adjusted under 35 U.S.C. 154(b) by 1434 days.

(21) Appl. No.: 12/329,848

(22) Filed: Dec. 8, 2008

(65) Prior Publication Data

US 2010/0145222 A1    Jun. 10, 2010

(51) Int. Cl.
| A61B 5/04 | (2006.01) |
| A61N 1/18 | (2006.01) |
| A61B 5/05 | (2006.01) |
| A61B 5/00 | (2006.01) |
| A61B 5/0488 | (2006.01) |

(52) U.S. Cl.
CPC ............... *A61B 5/05* (2013.01); *A61B 5/04001* (2013.01); *A61B 5/0488* (2013.01); *A61B 5/4893* (2013.01); *A61B 5/726* (2013.01); *A61B 5/7257* (2013.01)

(58) Field of Classification Search
CPC .......... A61B 5/4893; A61B 5/04001–5/04005; A61N 1/3605–1/36196
USPC ........................................ 600/547, 554, 546
See application file for complete search history.

(56) References Cited

U.S. PATENT DOCUMENTS

| 4,920,979 | A |   | 5/1990  | Bullara |
| 5,095,905 | A |   | 3/1992  | Klepinski |
| 5,125,406 | A |   | 6/1992  | Goldstone et al. |
| 5,215,089 | A |   | 6/1993  | Baker, Jr. |
| 5,284,153 | A | * | 2/1994  | Raymond et al. ............. 600/554 |
| 5,284,154 | A | * | 2/1994  | Raymond et al. ............. 600/554 |
| 5,375,594 | A |   | 12/1994 | Cueva |
| 5,775,331 | A | * | 7/1998  | Raymond et al. ............. 600/554 |
| 5,860,939 | A | * | 1/1999  | Wofford et al. ............... 600/587 |
| 6,081,371 | A |   | 6/2000  | Shioda et al. |
| 6,088,154 | A |   | 7/2000  | Morita |
| 6,132,387 | A |   | 10/2000 | Gozani et al. |
| 6,264,616 | B1 | * | 7/2001  | Don .............................. 600/559 |
| 6,266,182 | B1 |   | 7/2001  | Morita |
| 6,266,558 | B1 |   | 7/2001  | Gozani et al. |
| 6,306,100 | B1 | * | 10/2001 | Prass ............................. 600/554 |

(Continued)

FOREIGN PATENT DOCUMENTS

| WO | WO 2005013805 A2 * | 2/2005 |
| WO | WO 2006072050 A2 * | 7/2006 |

OTHER PUBLICATIONS

Litvak et al. "Auditory nerve fiber responses to electric stimulation modulated and unmodulated pulse trains" J. Acoust. Soc. AM. 110(1), Jul. 2001.*

(Continued)

*Primary Examiner* — Sean Dougherty
*Assistant Examiner* — Michael C Stout
(74) *Attorney, Agent, or Firm* — Dicke, Billig & Czaja, PLLC

(57) ABSTRACT

A nerve monitoring system facilitates monitoring an integrity of a nerve.

36 Claims, 13 Drawing Sheets

(56) References Cited

U.S. PATENT DOCUMENTS

| | | | |
|---|---|---|---|
| 6,308,105 B1 | 10/2001 | Duysens et al. | |
| 6,334,068 B1* | 12/2001 | Hacker | 600/545 |
| 6,379,313 B1 | 4/2002 | Gozani et al. | |
| 6,466,817 B1* | 10/2002 | Kaula et al. | 600/546 |
| 6,500,128 B2 | 12/2002 | Marino | |
| 6,507,755 B1 | 1/2003 | Gozani et al. | |
| 6,600,956 B2 | 7/2003 | Maschino et al. | |
| 6,661,571 B1 | 12/2003 | Shioda et al. | |
| 6,692,444 B2* | 2/2004 | Gozani et al. | 600/554 |
| 7,177,677 B2* | 2/2007 | Kaula et al. | 600/546 |
| 7,236,832 B2 | 6/2007 | Hemmerling et al. | |
| 7,452,335 B2* | 11/2008 | Wells et al. | 600/554 |
| 7,628,761 B2* | 12/2009 | Gozani et al. | 600/554 |
| 7,634,315 B2* | 12/2009 | Cholette | 607/2 |
| 7,846,094 B2* | 12/2010 | Miller | 600/301 |
| 2001/0055062 A1 | 12/2001 | Shioda et al. | |
| 2003/0093006 A1* | 5/2003 | Wells et al. | 600/547 |
| 2003/0135247 A1* | 7/2003 | Zierhofer | 607/60 |
| 2004/0070822 A1 | 4/2004 | Shioda et al. | |
| 2005/0020876 A1 | 1/2005 | Shioda et al. | |
| 2005/0075578 A1* | 4/2005 | Gharib et al. | 600/546 |
| 2005/0085743 A1* | 4/2005 | Hacker et al. | 600/554 |
| 2005/0182454 A1* | 8/2005 | Gharib et al. | 607/48 |
| 2005/0283090 A1* | 12/2005 | Wells | 600/544 |
| 2006/0020222 A1* | 1/2006 | Gozani et al. | 600/546 |
| 2006/0100540 A1* | 5/2006 | Gozani et al. | 600/554 |
| 2007/0021682 A1* | 1/2007 | Gharib et al. | 600/546 |
| 2007/0118047 A1* | 5/2007 | Tracey et al. | 600/554 |
| 2007/0282217 A1* | 12/2007 | McGinnis et al. | 600/546 |
| 2008/0071191 A1* | 3/2008 | Kelleher et al. | 600/554 |
| 2008/0263451 A1* | 10/2008 | Portele et al. | 715/727 |
| 2008/0300655 A1* | 12/2008 | Cholette | 607/60 |
| 2009/0030337 A1* | 1/2009 | Gozani et al. | 600/554 |
| 2009/0054804 A1* | 2/2009 | Gharib et al. | 600/554 |
| 2009/0105604 A1* | 4/2009 | Bertagnoli et al. | 600/546 |
| 2009/0177112 A1* | 7/2009 | Gharib et al. | 600/554 |
| 2010/0010367 A1* | 1/2010 | Foley et al. | 600/546 |

OTHER PUBLICATIONS

Journzal of Neurology, Neurosurgery, and Psychiatry, 1978, 41, 54-64 Refractory period studies in a human neuromuscular preparation J. Kopec, J. Delbeke, and A. J. McCOMAS2.*

W. Lamadee et al., "A new system for continuous recurrent laryngeal nerve monitoring," Minimally Invasive Therapy, 2007; 16:30; pp. 149-154.

Ruckenstein et al., "Advantages of a New, Atraumatic, Self-Retaining Electrode for Direct Cochlear Nerve Monitoring," Skull Base Surgery, vol. 7, No. 2, 1997, pp. 69-75.

Ulmer et al., "Real-time monitoring of the recurrent laryngeal nerve: An observational clinical trial," Surgery, vol. 143, No. 3, Mar. 2008, pp. 359-365.

Medtronic NIM—Neuro 2.0 Nerve Integrity Monitor, User's Guide 2005.

http://www.vnstherapy.com/depression/hcp/ForSurgeons/implanted.aspx, Aug. 1, 2007, pp. 1-4.

VNS Therapy, Implantation Procedure, Jul. 2006, pp. 1-24.

* cited by examiner

METHOD AND SYSTEM FOR MONITORING A NERVE

This application is related to U.S. application Ser. No. 12/329,813, filed on even date herewith, and entitled "Nerve Electrode"; the entire teachings of which are incorporated herein by reference.

BACKGROUND

The present disclosure relates to nerve stimulation and recording systems. In particular, it relates to electrodes adapted to stimulate nerves or record neurogenic responses.

In many invasive medical procedures, steps are taken to preserve healthy surrounding tissues while performing the procedure on a target tissue. In one example, in surgeries involving the head and neck, a surgeon must guard against unintentional damage to surrounding nerves while excising other tissue, such as a tumor. This damage may result from direct trauma (e.g. an incision) or "blind" trauma, such as stretching, torsion, compression, ischemia, thermal damage, electrical damage, or other surgical manipulations. Blind damage is of particular concern because the damage may be cumulative over the course of the surgery but may not be recognizable by the surgeon during the surgery.

One conventional technique of preserving the nerve includes the surgeon periodically applying a stimulation probe at the nerve and simultaneously measuring the neurogenic response from an associated innervated muscle via electromyography or other techniques. Accordingly, each time the surgeon desires to check the health or integrity of the nerve, the surgeon will maneuver the probe to contact the nerve, and apply the stimulation signal. After measuring and observing the response to the stimulus, the surgeon removes the probe from contact with the nerve.

Unfortunately, this conventional technique can lead to many inconsistencies. For example, it is difficult to establish accurate information about the response of an unimpaired nerve because the stimulation probe is placed in a slightly different location each time it is applied, resulting in a slightly different stimulus to the nerve. This contact variability in applying the stimulus leads to a slightly different response pattern. Accordingly, the slightly different locations of stimulation tend to cloud ascertainment of a normal or typical response of the innervated muscle (when the nerve is not impaired) and also cloud identification of a response signal that corresponds to an impairment or disturbance of the nerve. Moreover, because the stimulation probe is applied intermittently, there is no assurance whether the response signal is being measured at the time that the nerve is being impaired or being measured at the time the nerve is not being impaired.

Accordingly, the conventional techniques used during a medical procedure to monitor the health of a nerve fall short of the consistency and accuracy that would be desirable to reliably ascertain the integrity of the nerve during surgery.

DETAILED DESCRIPTION

Figure 1A:
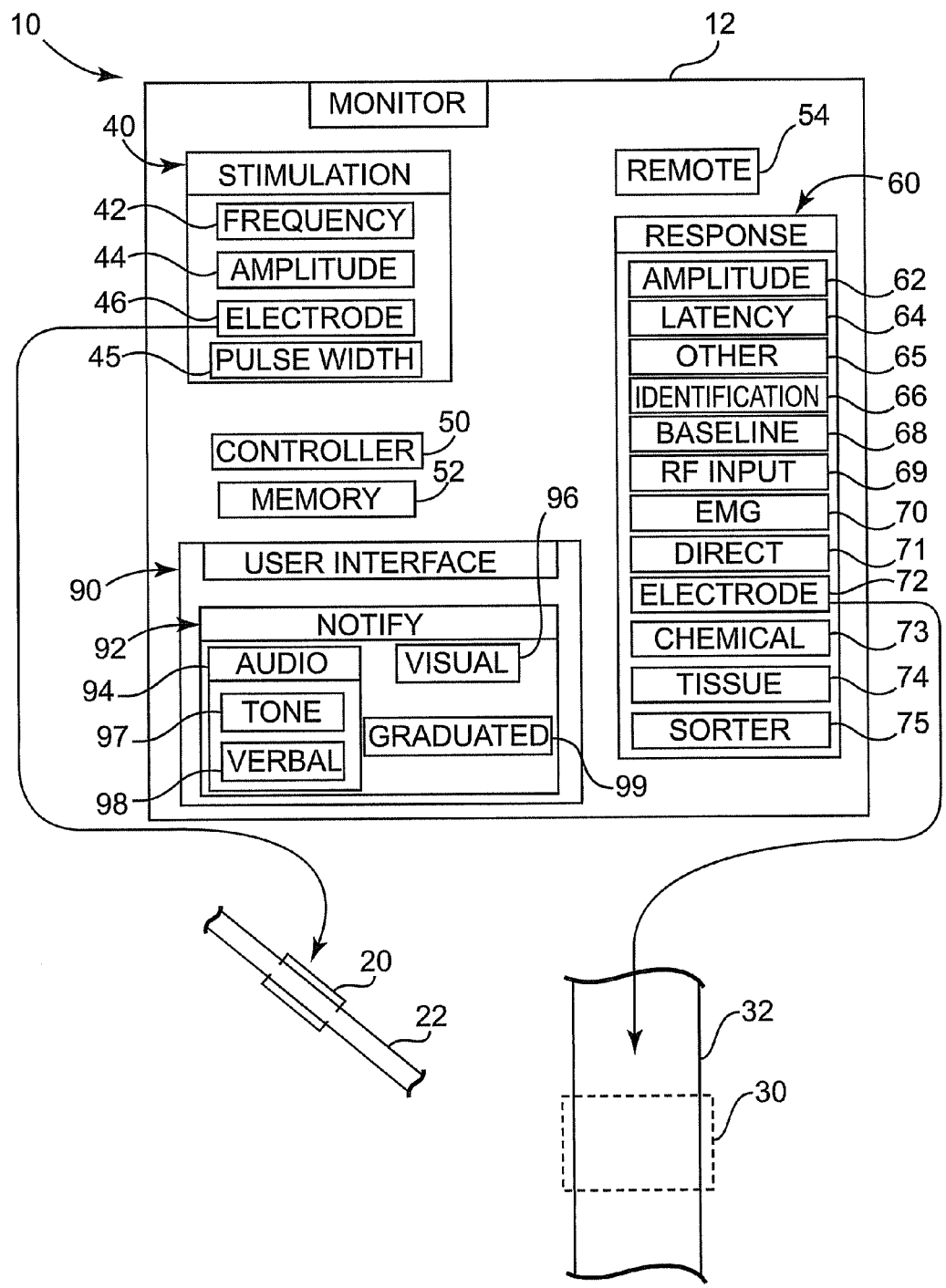
FIG. 1A is a schematic illustration of a nerve condition monitoring system and including a block diagram of a nerve monitor, in accordance with principles of the present disclosure.
Figure 1B:
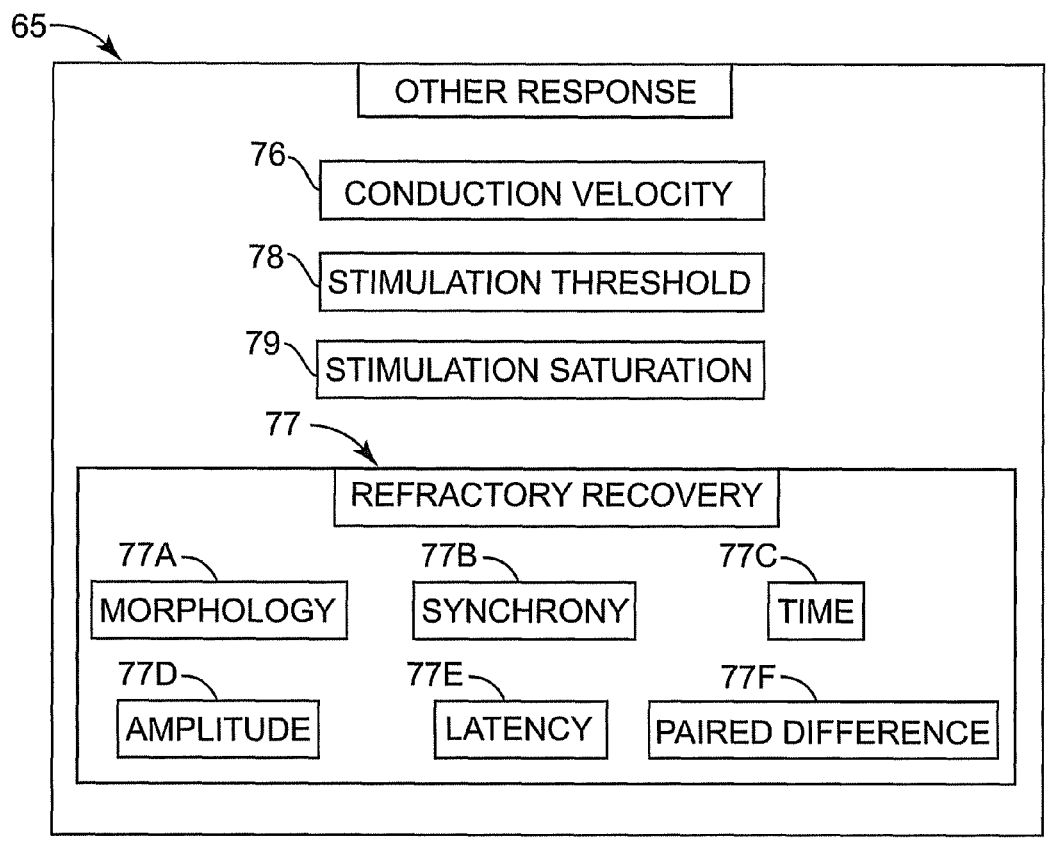
FIG. 1B is a block diagram of a response module of a nerve monitor, in accordance with principles of the present disclosure.

Embodiments of the present disclosure are directed to electrically monitoring a nerve during a surgical procedure on a target tissue that is in the vicinity of the nerve. In general terms, the method includes removably securing a cuff electrode about the nerve adjacent to the target tissue and then establishing a baseline neurogenic response by applying a series of stimulation signals to the nerve via the cuff electrode. In some embodiments, the neurogenic response is recorded (e.g., measured) at the innervated muscle via electromyography, while in other embodiments, the neurogenic response is recorded at the nerve as a direct nerve potential. In yet other embodiments, other known neuro-monitoring techniques are employed to measure and record the result of neurogenic stimulation or to measure and record a response on a body tissue. For example, in one non-limiting example, the neurogenic response is measured and recorded via chemical-based biometrics, such as tracking levels of gastric acid, perspiration, or chlorides that are indicate of whether or not a nerve is impaired. In another non-limiting example, the potential impairment of a nerve is monitored by measuring and recording the neurogenic response via other biometrics, such as monitoring rhythmic contraction of smooth muscles to move contents through the digestive tract (commonly referred to as peristalsis).

In one aspect, this baseline response generally corresponds to the state of the nerve prior to any potential impairment related to the surgical procedure. Accordingly, after establishing this baseline response pattern, the surgical procedure is performed on the target tissue while automatically stimulating (via the cuff electrode) the nerve with a stimulation signal at periodic intervals. Upon comparing a measured neurogenic response to a periodic stimulation signal relative to the baseline neurogenic response pattern, one can determine whether the health of the nerve is being impaired.

With this in mind, in some embodiments, the term neurogenic refers to a neural-related response or activity initiated by natural neural processes while in other embodiments, the term neurogenic refers to a neural-related response or activity initiated by an external stimulus, such as, but not limited to an evoked potential stimulus. In yet other embodiments, the term neurogenic refers to a neural-related response or activity caused by both a naturally neural process and an external stimulus. In some embodiments, the term nerve refers to neuro structures in general or some specific neuro structures, including (but not limited to) one or more of an entire nerve, a nerve fiber, multiple nerve fibers, an axon, spatial grouping of axons, or a functional grouping of axons within the nerve.

One non-limiting example of automatically monitoring a nerve during a surgical procedure includes monitoring a vagus nerve during a surgery of the head and/or neck. For example, in surgeries affecting the thyroid gland, one embodiment of the present disclosure includes removably securing a cuff electrode about a nerve, such as the vagus nerve or its branches, like the recurrent laryngeal nerve and superior laryngeal nerve. In particular, the cuff electrode is placed around the vagus nerve within the carotid sheath with the cuff electrode located proximal or adjacent (relative to the brain stem) to the distal site of the surgical procedure (e.g., tumor removal). In addition, in some embodiments, an EMG-based endotracheal tube electrode or another type of insertable measurement electrode(s) is removably inserted adjacent the vocal cords and/or other muscles innervated by the nerve to be monitored. In other embodiments, a monitoring electrode, such as a cuff electrode, is placed about the nerve at a point spaced apart from the location at which the stimulation is applied.

With the cuff electrode securely positioned about the nerve, the monitor automatically stimulates the nerve at periodic intervals (e.g., from less than one second to greater than 60 seconds, and in-between) and the monitor tracks the neurogenic response. In one aspect, the surgeon can select the frequency of intervals at which the nerve is stimulated and adjustment of periodic intervals can be based on the urgency of the monitoring. A control of the periodic interval selection includes a slow stimulation rate (e.g., every 60 seconds or less often), fast stimulation rates (e.g., every second or more often), and intermediate rates between the slow rate and the fast rate. In one non-limiting example, faster stimulation rates are used during surgical periods in which there is a greater risk to neurologic structures and slower stimulation rates are used during surgical periods posing with less risk. With this arrangement, stimulation to the nerve is applied no more than necessary in order to avoid potential fatigue of the nerve or muscle In one aspect, possible nerve impairment (e.g., due to stretching or manipulation) is identified by one measured neurogenic response or a series of measured neurogenic responses that differ from a baseline neurogenic response pattern. These differences are tracked and the surgeon is automatically notified via graphical alarm information (e.g., trending patterns, threshold, etc.) and/or audible alarm information when a limit has been exceeded. In one aspect, the audible alarm comprises a graduated alarm in which a volume of the alarm is in proportion to a level of deviation of the measured neurogenic response from the baseline neurogenic response pattern. Of course, at any time the surgeon can choose to visually monitor the graphical information even when no alarm has been triggered. In one example, a decrease (or trend of decreases) in amplitude and/or increase in latency from the baseline response beyond a predetermined or user-defined limit (or criteria) may indicate deteriorating vagus nerve quality, and upon providing automatic notification to the surgeon enable the surgeon to take actions to alleviate the nerve impairment.

In some embodiments, a potential nerve impairment is automatically identified by observing a neurogenic response waveform without reference to a baseline response pattern. In these embodiments, an overall morphology pattern, synchrony pattern, amplitude, or latency of the neurogenic response includes recognizable irregularities indicative of nerve impairment. For example, in the context of a synchrony pattern, such irregularities are observable as a response waveform having many peaks or humps where one or few peaks or humps are expected. In another non-limiting example, other irregularities include several peaks or humps having substantially different peak values instead of substantially similar peak values or instead of substantially harmonious peak values. These disrupted synchrony waveform patterns would be indicative of a disorganized response by the various axons or motor units of the nerve and therefore indicative of nerve impairment. Accordingly, by recognizing certain signatory patterns indicative of nerve dysfunction, these embodiments can automatically identify nerve impairment without reference to a measured baseline response pattern on the monitored nerve.

It is understood that embodiments of the present disclosure are not limited to monitoring the vagus nerve but apply to other cranial nerves, spinal nerves, or peripheral nerves. This monitoring can be applied to motor (Efferent) nerves, sensory (Afferent) nerves, and/or mixed nerve fiber situations for the somatic and autonomic nervous systems. Moreover, while the electrode is described above in the context of evoked potential monitoring of nerves during a surgical procedure, it is understood that in some embodiments, the electrodes of the present disclosure also are employable with implantable stimulators, to provide therapies associated with stimulating other target nerves, including but not limited to, the vagus nerve.

In some embodiments, the cuff electrode employed in monitoring the nerve comprises an elongate body and a cuff portion. The cuff electrode is configured to be removably secured to the nerve to enable stable positioning of the cuff electrode during the surgical procedure. In one embodiment, the cuff portion includes a pair of generally curved fingers that are slidably engageable in a side-by-side relationship. In particular, the fingers are configured to releasably engage each other in a closed position to define a lumen that automatically self adjusts to the proper size to encircle the nerve. The cuff portion is also configured with a hinge mechanism at a base of the fingers such that application of a pressing or squeezing force on a tab (relative to the elongate body) adjacent the hinge portion causes the fingers to separate away from each other with their distal tips spaced apart, resulting in an open position of the cuff portion. When in this open position, cuff portion is readily mounted onto, or readily removed from, the nerve.

In another embodiment, the nerve electrode comprises an elongate body and a cuff portion. In one aspect, the cuff portion includes a generally arcuate nerve contact portion of the elongate body and a single flexible, resilient arm that extends from the elongate body. In an open position, the arm is free to be slidably maneuvered underneath a nerve and around the nerve so that the nerve contact portion (of the elongate body) and a proximal portion of the arm define a lumen encircling the nerve. In a further aspect, a distal portion of the arm is slidably advanced into a recess of the electrode body to removably secure the proximal portion of the arm in the closed position relative to the nerve contact portion of the elongate body.

By removably securing a nerve electrode (of one of the embodiments of the present disclosure) relative to a target nerve and monitoring the ensuing neurogenic response, a surgeon can achieve and maintain a hands-free, automatic continuous (or substantially continuous) monitoring of the health and integrity of a nerve in a reliably consistent manner during a surgical procedure.

These embodiments, and other embodiments, are described more fully in association with FIGS. 1A-14.

A nerve monitoring system 10 is shown in FIG. 1A, in accordance with principles of the present disclosure, and comprises a stimulation electrode 20, a response electrode 30 and a monitor 12 that includes at least a stimulation module 40 and a response module 60. In general terms, the stimulation module 40 of monitor 12 applies a stimulation signal to nerve 22 via stimulation electrode 20 while response module 60 of monitor 12 measures a neurogenic response signal at muscle 32 via measurement electrode 30 (or at nerve 22 via measuring a direct action potential with a second cuff electrode similar to and spaced apart from electrode 20). The response is communicated to the surgeon via a user interface 90 of the monitor 12. Accordingly, by using monitor 12, a surgeon can inferentially determine the relative health and function of a nerve by stimulating that nerve and measuring a corresponding neurogenic response at muscle 32 or at nerve 20.

With the above general construction of system 10 in mind, nerve stimulation monitor 12 is further described. In doing so, it is understood that the features and components of the monitor 12 can be arranged in many different forms and groupings, and therefore monitor 12 is not strictly limited to the particular arrangement or groupings of functions illustrated in FIG. 1A. Nevertheless, in the illustrated embodiment, monitor 12 additionally comprises a controller 50, memory 52, and the previously mentioned user interface 90.

In one aspect, user interface 90 of monitor 12 comprises a graphical user interface or other display that provides electronic control touchpad features, and as such, monitor 12 provides for the simultaneous display and/or activation of the modules (e.g., stimulation module 40, response module 60, etc.), functions, and features of monitor 12 described in association with FIG. 1A. In other embodiments, user interface 90 includes one or more thumbwheels, buttons, or other electromechanical control mechanisms for implementing one or more the functions of the nerve monitoring system 10. In some embodiments, system 10 includes a remote control 54 that is in wired or wireless communication with monitor 12 and that enables a user to control at least some of the modules, functions, and/or features controllable normally via user interface 90 but at a distance spaced apart from monitor 12.

In some embodiments, user interface 90 includes a notify function 92 which enables the user to select a preferred format (e.g., graphical, audible, mixed) by which they will receive information about potential nerve impairment. In one aspect, the notify function 92 communicates information according to one or more specific parameters tracked via an identification function 66 that will be described later in more detail in association with response module 60 of FIG. 1A. In some embodiments, via visual function 96, the notify function 92 provides graphical reports of trends in the parameters of a neurogenic response signal to enable the user (e.g., a surgeon) to identify whether potential nerve impairment is increasing or decreasing depending upon the particular action taken during the surgical procedure. In some embodiments, either apart from or in combination with visual function 96, user interface 90 comprises an audio function 94 configured to provide audible alerts to one or more different reports provided by the monitor 12. Among other reporting functions, the audio function 94 provides an audible alert when response module 60 has identified potential impairment of the nerve being monitored. In one embodiment, based on the measured neurogenic response, the audio function 94 provides a faster rate or higher volume of audible sounds to indicate increased potential for impairment of the nerve being monitored and a lower rate or lower volume of audible sounds to indicate decreased potential for impairment of the nerve being monitored. In this way, notify function 92 of monitor 12 provides direct, ongoing feedback to the surgeon on whether their current course of actions are improving or impairing the health of the nerve.

In one aspect, the audio function 94 provides information distinct, and independent from, a conventional acoustic feedback signal reported via electromyography. In other embodiments, this acoustic feedback signal is made selectively available via audio function 94 in addition to the types of automatic audio or graphical notification previously described above.

In one embodiment, controller 50 comprises one or more processing units and associated memories configured to generate control signals directing the operation of monitor 12 of system 10. In particular, in response to or based upon commands received via user interface 90 and/or instructions contained in the memory 52 associated with controller 50, controller 50 generates control signals directing operation of stimulation module 40 and/or response module 60.

For purposes of this application, in reference to the controller 50 the term "processing unit" shall mean a presently developed or future developed processing unit that executes sequences of instructions contained in a memory. Execution of the sequences of instructions causes the processing unit to perform steps such as generating control signals. The instructions may be loaded in a random access memory (RAM) for execution by the processing unit from a read only memory (ROM), a mass storage device, or some other persistent storage, as represented by memory 52. In other embodiments, hard wired circuitry may be used in place of or in combination with software instructions to implement the functions described. For example, controller 50 may be embodied as part of one or more application-specific integrated circuits (ASICs). Unless otherwise specifically noted, the controller is not limited to any specific combination of hardware circuitry and software, nor limited to any particular source for the instructions executed by the processing unit.

In one embodiment, monitor 12 includes at least substantially the same features and attributes as the nerve integrity monitor (NIM) described and illustrated in assignee's U.S. Pat. No. 6,334,068, titled INTRAOPERATIVE NEURO- ELECTROPHYSIOLOGICAL MONITOR, and which is hereby incorporated by reference in its entirety.

Referring again to FIG. 1A, stimulation module 40 of monitor 12 includes a frequency function 42, an amplitude function 44, a pulse width function 45, and an electrode function 46. In one aspect, the frequency function 42, amplitude function 44, and pulse width function 45 enable user selection and tracking of the frequency, the amplitude, and the pulse width, respectively, of a stimulation signal. In another aspect, the electrode function 46 enables user selection and tracking of stimulation of nerve 22 via nerve electrode 20. In one embodiment, nerve electrode 20 comprises a cuff-type electrode, as schematically illustrated in FIG. 1A. More specific embodiments of nerve electrode 20 are described and illustrated in more detail in association with FIGS. 2-7 and 9-14.

As illustrated in FIG. 1A, response module 60 of monitor 12 includes one or more of an amplitude function 62, a latency function 64, an other response parameter function 65, an identification function 66, a baseline function 68, an RF input function 69, an EMG function 70, a direct nerve measurement function 71, an electrode function 72, a chemical-based biometric function 73, a tissue-based biometrics function 74, and an impairment sorter 75.

In one aspect, the EMG function 70 enables user control over measuring the response of the muscle via electromyography. In another aspect, via direct function 71, responses are measured at the stimulated nerve as a direct action potential. In cooperation with the EMG function 70, the electrode function 72 controls measuring response of muscle 32 via measurement electrode 30. In one embodiment, measurement electrode 30 comprises a typical EMG electrode (e.g., an endotracheal tube electrode), which is schematically illustrated in FIG. 1A via dashed lines 30. In one aspect, in cooperation with the EMG function 70, the amplitude function 62 and latency function 64 enable tracking of the amplitude and the latency, respectively, of the response signal measured at muscle 32 via EMG function 70.

In some embodiments, monitor 12 includes RF input function 69, which in general terms, is configured to receive radiofrequency input associated with a monopolar or bipolar electrocautery device used in the surgical procedure adjacent the monitored nerve. During the surgical procedure, the electrocautery device can indirectly damage adjacent nerves via local heating effects. In addition, direct electrocautery will sever and destroy tissue. Accordingly, variations in the degree of heating of the adjacent nerves can cause various levels of nerve injury as the electrocautery device contacts its target tissue. Therefore, tracking when an electrocautery device is being used is helpful in determining whether impairment of the nerve is caused by electrocautery of tissue adjacent the monitored nerve. If the electrocautery device is determined to be the likely cause of the impairment, then the surgeon can modify their procedure to avoid further impairment to the nerve.

With this in mind, as the electrocautery device is operated it emits radiofrequency signals which can be tracked and are indicative of when and how the electrocautery device is being used. Accordingly, in this one embodiment, RF input function 69 receives RF signals associated with activity of the electrocautery device. In some embodiments, the RF signals are obtained via a muting detector feature of monitor 12 when monitor 12 includes one or more features and attributes of a monitor having substantially the same features and attributes as the previously identified U.S. Pat. No. 6,334,068. In this example, the muting detector mechanism is inductively clamped to an electrocautery probe and therefore the muting detector mechanism captures an RF signal representing the activity of the electrocautery device. In this way, the RF signal associated with the activity of the electrocautery device is provided to RF input function 69 to monitor 12.

With the availability of the RF signal via RF input function 69, monitor 12 substantially continuously checks to see if a detected impairment to the monitored nerve is occurring synchronously with (i.e., at the same time as) heightened activity of the electrocautery device when the electrocautery device is near the nerve. Accordingly, at the same time that RF input function 69 is tracking the electrocautery activity, other mechanisms described herein for measuring a neurogenic response (to an evoked potential or stimulation signal) are used to detect whether an impairment is occurring. For example, in some embodiments, the impairment is detected by measuring a neurogenic response at an innervated muscle via electromyography, at the nerve as a direct nerve potential, via chemical-based biometrics, or via smooth muscle monitoring, as further described herein in association with FIG. 1A.

Consequently, using both the RF input function 69 and detected impairments, monitor 12 determines whether or not a given impairment is likely being caused by an electrocautery device.

In some embodiments, instead of capturing RF signals via the muting detector, the RF signals are obtained via other patient leads connected to monitor 12 that are suitable for picking up RF signals and generally tracking activity of the electrocautery device.

A further description of identifying nerve impairment caused by electrocautery activity is described later in more detail in association with verbal function 98 of FIG. 1A and in association with assessment module 110 of FIG. 1D.

However, prior to measuring a neurogenic response of the target nerve during a surgical procedure, a user employs the baseline function 68 of the response module 60 to determine a baseline neurogenic response pattern via measurements taken at the innervated muscle 32 or at the nerve 22 upon stimulating nerve 22. In other words, before attempting to determine whether the integrity of the target nerve is being impaired, the baseline function 68 is employed to determine the response signal or pattern (via amplitude function 62, latency function 64, or other parameters further described later in association with other response function 65) that normally occurs in the absence of a potential nerve impingement during a surgical procedure.

In some embodiments, the response module 60 employs identification function 66 of the response module 60 and notify function 92 of user interface 90 to enable the monitor 12 to automatically notify the user when a parameter (e.g., amplitude) of the measured response signal differs from a predetermined limit, such as preset percentage of the baseline response signal (e.g., 25%, 50%, 75%) or some other user defined setting, criteria, or value.

For example, in some embodiments, the identification function 66 tracks and identifies changes in parameters of the measured response signal relative to the baseline response pattern. These changes in parameters tracked via the identification function 66 include, but are not limited to one or more of: (1) one or more decreases in amplitude; (2) one or more increases in latency; or (3) a decrease in an amplitude-based energy (i.e., the area of) of the measured response curve.

In further reference to FIG. 1, in some embodiments, response module 60 also includes the chemical-based biometrics function 73 configured to measure a neurogenic response (in response to stimulation of a target nerve) via chemical-based biometrics, such as tracking levels of gastric acid, perspiration, or chlorides that are indicate of whether or not a particular nerve is impaired. In some embodiments, response module 60 also includes the tissue-based or smooth muscle-based biometrics function 74 configured to measure a neurogenic response (in response to stimulation of a target nerve) via tissue-based biometrics (or smooth muscle based biometrics), such as monitoring rhythmic contraction of smooth muscles to move contents through the digestive tract (commonly referred to as peristalsis).

In further reference to FIG. 1, in some embodiments, the identification function 66 tracks and identifies changes in parameters of the measured response signal (relative to the baseline response pattern) according to the other response parameter function 65, separately from or in combination with amplitude function 62, latency function 64, and/or an energy parameter (as part of the amplitude function 62). For example, as schematically illustrated in FIG. 1B, these changes in parameters tracked via the identification function 66 include, but are not limited to one or more of: (1) a nerve refractory recovery parameter 77 configured to identify one or more changes in a nerve recovery refractory waveform (as explained in more detail below); (2) a nerve conduction velocity parameter 76 configured to identify one or more changes in a nerve conduction velocity function; (3) a nerve stimulation threshold parameter 78 configured to identify one or more changes in a nerve stimulation threshold (e.g., the amount of stimulation at which the nerve begins to produce an observable neurogenic response); or (4) a nerve stimulation saturation parameter 79 configured to identify one or more changes in a nerve stimulation saturation threshold (e.g., the point at which the nerve response signal does not further increase with further increased levels of stimulation).

In some embodiments, the nerve refractory recovery parameter 77 identifies a potential nerve impairment by monitoring a response of the nerve to a paired stimuli (also know as a paired difference stimulus or a t-test stimulus) which applies a pair of identical stimulus signals to an axon (or a group of axons defining a nerve) separated by a fixed time delay. In one aspect, this monitoring method is used to provide increased sensitivity in measuring neurogenic response properties because of neuronal injury.

In some embodiments, monitoring a neurogenic response to such paired stimuli protocols includes observing or measuring changes in at least one of an overall response waveform morphology 77A, a synchrony waveform pattern 77B, an double response time 77C (e.g., the time between consecutive responses), an amplitude 77D, or a latency 77E of the response to the second stimulus by itself and/or relative to the response to the first stimulus. In some embodiments, this method includes applying a series of paired stimuli in which the initial time delay (between the first stimulus pulse and the second stimulus pulse) is equal to or greater than the natural refractory recovery period (the time taken for the nerve to fully recovery before a second stimulus is applied). Thereafter, the monitoring of the nerve is performed continually as the time delay between the consecutive first and second stimuli is gradually decreased (in each successive application of the pair stimuli) to be less than the natural refractory recovery period. By driving the time delay to lower and lower values, the monitor 12 can determine the health of the nerve based on how the nerve responds to the decreasing time delay between consecutive pulses.

In one aspect, in the context of applying a paired stimuli, the overall response waveform morphology 77A illustrates and identifies the extent to which some form of nerve impairment has occurred or is occurring based on one or more portions (e.g., response pulse width, response pulse peak, rate of increase to pulse peak, multiple peaks, absence of significant peak, etc.) of the waveform morphology substantially differing from a known response waveform pattern for that type of nerve. Upon recognizing this altered or abnormal morphology, the refractory recovery parameter 77 indicates the likelihood of nerve impairment.

In another aspect, in the context of applying a paired stimuli, the synchrony waveform pattern 77B illustrates and identifies the extent to which the axons or motor units of a nerve respond together in an organized manner or synergistic fashion. In other words, in the absence of nerve impairment, the waveform of the neurogenic response will have a recognizable pattern that corresponds to normal nerve function, as would be recognized by those skilled in the art. However, when the nerve is impaired, the axons of the nerve will respond in a disorganized manner (e.g., a dissynchronous manner), producing substantial irregularities indicative of the various axons responding separately from each other, with some axons not responding at all, some axons responding with a weaker response signal, some axons responding at the wrong time, etc. Accordingly, the synchrony waveform pattern 77B is configured to indicate nerve impairment via automatically recognizing at least a portion of a neurogenic response pattern that includes multiple perturbations or erratic characteristics (e.g., many smaller humps instead of a single integrated hump) where a generally smooth or predictable waveform would otherwise be expected.

In some embodiments, operation of the nerve refractory recovery function 77 includes monitoring changes in the refractory recovery period on a segmented basis. In other words, consecutive segments within a single neurogenic response waveform are compared with each other to observe changes in waveform morphology, synchrony waveform patterns, amplitude, or latency from segment-to-segment that would be indicative of nerve impairment.

In some embodiments, the nerve refractory recovery parameter 77 is configured to perform a comparison of the neurogenic response to the first stimulus relative to the neurogenic response to the second stimulus of the paired stimuli (having a fixed time delay between the consecutive stimulation pulses), as represented by paired difference parameter 77F. In this comparison, an algebraic subtraction is performed in which the second response waveform (i.e., the response to the second stimulus) is inverted relative to the first response waveform (i.e., the response to the first stimulus) and then a subtraction is performed of corresponding data points of the second response waveform from the first response waveform. When little or no difference is observed based on this algebraic subtraction, then there is little or no likelihood of potential nerve impairment. However, if the comparison via the algebraic subtraction results in a one or more large observed differences or in many smaller observable substantial differences, then there is a likelihood of potential nerve impairment. Accordingly, this comparison provides a derived response pattern and may be referred to as a paired-difference-response (PDR).

In one aspect, changes in neuronal response observed according to operation of the nerve refractory recovery parameter 77 as described above provide feedback information to the surgeon to indicate that one or more types of nerve impairment is occurring. These types of impairment include, but are not limited to, compression, traction (i.e., tension), heat injury, or a composite impairment. In one aspect, the type or degree of impairment is recognized via the observed changes in the morphology waveform, synchrony waveform pattern, amplitude, latency, or elapsed time (as described above), wherein the observed changes are associated the various sub-populations of axons arranged concentrically within a diameter of the nerve and/or the degree of myelinization of the axonal elements.

Figure 1C:
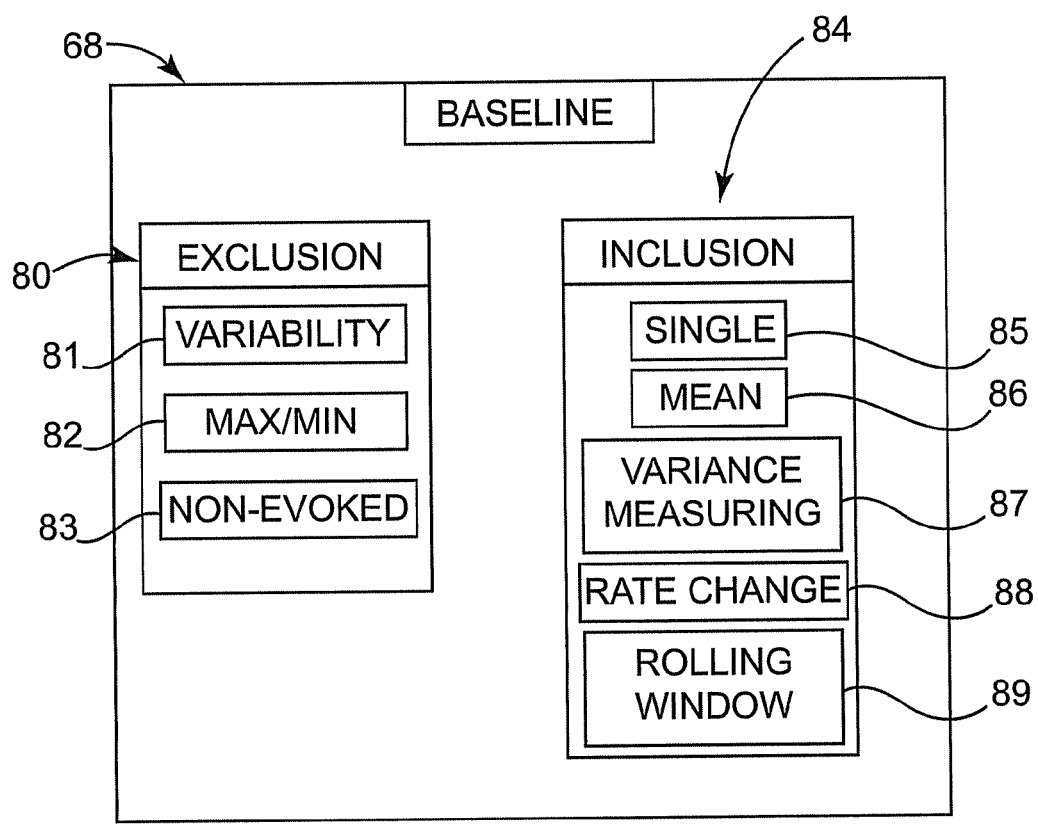
FIG. 1C is a block diagram of a baseline module of a nerve monitor, in accordance with principles of the present disclosure.

In one aspect, these other response parameters 76-79 associated with function 65 provide the capability to detect more subtle changes in a neurogenic response (that might not otherwise be recognized via tracking more conventional response parameters), which in turn, may detect the development for potential nerve impairment long before it becomes readily apparent via conventional monitoring of nerve integrity during a surgical procedure. For example, in another aspect, these other response parameters (according to other response parameter function 65) provide more discriminating information that would otherwise be available via conventional acoustic feedback from an innervated muscle, and thereby enable quicker and more effective detection of potential nerve impairment. In some embodiments, the baseline response pattern tracked via baseline function 68 is based on (or derived from) one or more of the following screening parameters of neurogenic responses (measured in the absence of potential impingement) according to an exclusion function 80 as schematically illustrated in FIG. 1C. These parameters include, but are not limited to: (1) a variability parameter 81 configured to apply a selective exclusion of some responses of multiple evoked neurogenic responses based on a degree of variability of the multiple responses; (2) a maximum/minimum parameter 82 configured to apply a selective exclusion of a maximum value and/or a minimum value of multiple evoked neurogenic responses; or (3) a non-evoked parameter 83 configured to apply a selective exclusion of artifacts, such as any non-evoked neurogenic responses or other artifacts not indicative of an evoked neurogenic response.

In some embodiments, the baseline response pattern tracked via baseline function 68 is based on (or derived from) one or more of the following screening parameters of neurogenic responses (measured in the absence of potential impingement) according to an inclusion function 84 as schematically illustrated in FIG. 1C. These parameters include, but are not limited to: (1) a single response parameter 85 configured to enable selective use of a single evoked response or of multiple evoked responses; (2) a statistical mean parameter 86 configured to use a statistical mean of multiple evoked neurogenic responses; (3) a variance measuring parameter 87 configured to use variance measuring (e.g., standard deviation) of multiple evoked neurogenic responses; (4) a rate change parameter 88 configured to use a rate of change of a series of evoked neurogenic responses; or (5) a rolling window parameter 89 configured to use a continuous sequence (or rolling window) of evoked neurogenic responses. In one aspect, the rolling window parameter 89 monitors a generally constant number of evoked neurogenic responses (e.g., 5, 10, or 15) and continually adds one or more new responses to the set or window while removing the oldest one or more responses from the set or window. In this manner, the most recent set (e.g., 5, 10, or 15) of responses are always in the monitoring window. In some embodiments, the monitoring window includes responses in series to help observe trends, while in other embodiments, the monitoring window includes an average of the responses in the window, which is more akin to a rolling average.

In some embodiments, one or more parameters of the baseline function 68 are identified via a Poisson distribution, as further described later in association with tools module in FIG. 1D.

In one aspect, these screening parameters of baseline response pattern function 68 are used to establish a baseline response pattern that is more indicative of a typical baseline neurogenic response than would otherwise be ascertained without the sorting process enabled via one or more of the identified screening parameters. In other words, these screening parameters help to ensure that a legitimate difference of the measured response signal (relative to a baseline response pattern) is identified because the screening parameters enable removing components from the baseline response pattern that are atypical within a sample of multiple evoked responses.

Referring again to FIG. 1A and keeping in mind the parameters tracked via the baseline function 68 and via the identification function 66, in one example, the identification function 66 is used to set an alarm limit relative to the baseline response pattern. In this arrangement, an amplitude of the measured response signal (during the surgical procedure) that is less than the alarm limit would trigger a notification of potential nerve impairment via notify function 92. Likewise, in another example, the identification function 66 is used to set a latency limit relative to the baseline response signal or pattern such that a latency of the measured response signal (during the surgical procedure) that exceeds the latency limit would trigger a notification of potential nerve impairment via notify function 92. In still other examples, similar limits are arranged to trigger the notify function 92 based on a limit (e.g., criteria, threshold, value) set according to any one or more of the previously identified parameters of the identification function 66.

In one aspect, this notification is communicated to the user via user interface 90 graphically via visual function 96 and/or audibly via audio function 94 of user interface 90, as previously described. In some embodiments, the audio function 94 comprises a tone function 97 and/or a verbal function 98. As just one example, audio function 94 of monitor 12 enables a surgeon to be notified of potential impingement of a target nerve without requiring the surgeon to look away from their procedure. This audible notification signal provides an immediate "no-look" feedback to the surgeon, thereby enhancing their concentration on the surgical procedure instead of being distracted with conventional techniques of monitoring a nerve. Moreover, because the electrode 20 is secured about nerve 22, the visual function 96 or the audio function 94 of the notify function 96 enable the surgeon to monitor the target nerve in a hands-free manner, thereby further enhancing their freedom to carry out the main procedure on the target tissue. In some embodiments, the alarm provided via the tone function 97 (of the audio function 94) is configured to emit several different types of tones such that each different type of tone corresponds to a relative degree of deviation of the measured neurogenic response from the baseline neurogenic response pattern. In other words, different tones represent different amounts of deviation from the baseline neurogenic pattern.

In some embodiments, audio function 94 includes verbal function 98 which is configured to provide a notification in the form of a verbal expression, such as the known words, to the surgeon to inform them of the condition of the nerve, such as "normal", "impairment", etc. In some embodiments, this verbal function 98 is configured to audibly identify the type of impairment that is occurring through the use of words such as "tension", "compression", etc. In some embodiments, the verbal function 98 is configured to identify the intensity of impairment through the use of words such as "low", "moderate", and "severe". Operation of the verbal function 98 is later described in more detail in cooperation with an impairment sorter 75 that is illustrated and described in association with FIG. 1D.

In further reference to FIG. 1A, in some embodiments, the alarms provided via the audio function 94 or the visual function 96 comprise a graduated alarm function 97 in which a volume of the alarm (audible or graphical) is in proportion to a degree of deviation of the measured neurogenic response from the baseline neurogenic response pattern.

Figure 1D:
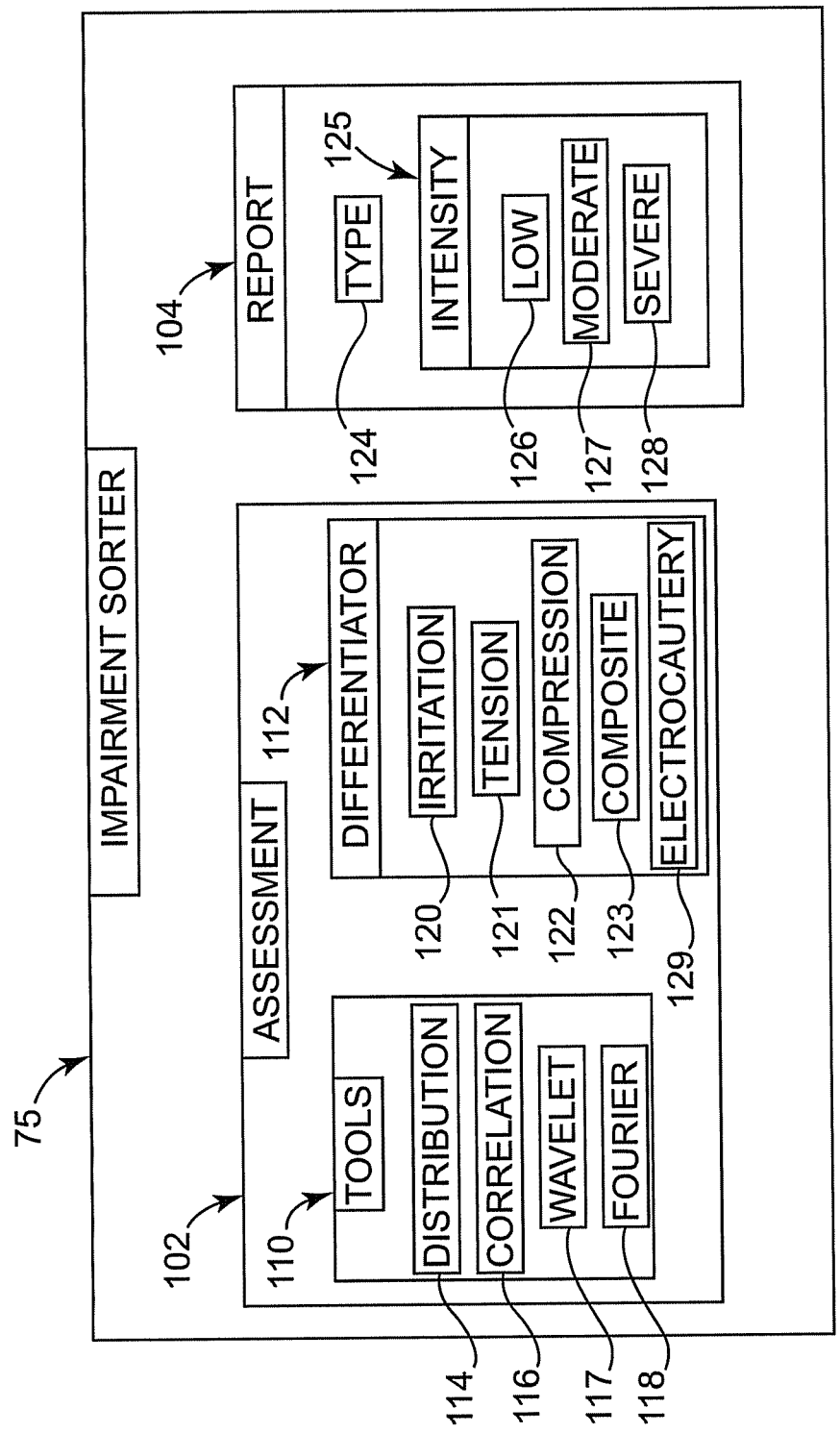
FIG. 1D is a block diagram of an impairment sorter of a nerve monitor, in accordance with principles of the present disclosure.

In some embodiments, the response module 60 includes an impairment sorter 75, which is further illustrated in FIG. 1D. As shown in FIG. 1D, impairment sorter 75 includes an assessment module 102 and a report module 104.

In general terms, the report module 104 operates in cooperation with the notify function 92 of user interface 90 and is configured to report the condition of the monitored nerve to the surgeon. In some embodiments, the report module 104 includes a type function 124 and an intensity function 125. In general terms, the type function 124 indicates the type of damage identified via the differentiator function 112, such as whether the nerve is experiencing minor irritation, tension, compression, a composite impairment of both tension and compression, or impairment directly or indirectly caused by electrocautery (as previously described in association with RF input function 69 in FIG. 1A).

Accordingly, when there is some impairment of the monitored nerve, then the type of impairment is communicated via verbal function 98 as one or more verbal expressions (e.g., words like tension, compression, etc.) in real-time to the surgeon during surgery.

In general terms, the intensity module 125 of the report module 104 is configured to provide an indication (via verbal function 98 of notify function 92 in FIG. 1) to the surgeon of the relative intensity of the impairment of the nerve. In one embodiment, the intensity module 125 includes a low function 126, a moderate function 127, and a severe function 128. Accordingly, when there is some impairment of the monitored nerve, then any such impairment is communicated via verbal function 98 as a verbal expression in real-time to the surgeon during surgery. In one aspect, such verbal expressions include, but are not limited to, the words low, moderate, or severe or other similar meaning words that indicate a relative degree of intensity. Further, in some embodiments, intensity function 125 provides and communicates at least two different levels of intensity.

In some embodiments, the assessment module 102 of impairment sorter 75 includes a tools module 104 and a differentiator module 112. In general terms, the tools module 110 is configured to apply different forms of statistical analysis and/or other filters to sort data of one or more measured neurogenic responses. In cooperation with differentiator 112, the tools module 110 removes noise while transforming the data to more accurately identify changes in nerve function with such changes including changes in amplitude, latency, or other enumerated aspects of nerve function previously described in association with identification function 66 in FIG. 1. Recognition of these changes from response-to-response or over time through multiple responses provides an indication of the type or extent of impairment to a nerve.

In one embodiment, the tools module 110 includes a distribution function 114, a correlation function 116, a wavelet function 117, and a Fourier function 118.

In one embodiment, the distribution function 114 is configured to recognize which type of statistical distribution that best characterizes neurogenic responses (for example, EMG responses) resulting from stimulation pulses. In one example, the neurogenic responses fit best within a Poisson distribution and therefore observations regarding the neurogenic response information is calculated from the Poisson distribution. However, other distributions are not excluded. In a few non-limiting examples, by using the Poisson distribution the mean of the received data provides a measure of the average delay while a standard deviation provides a measure the degree to which the responses are erratic. As another example, changes in the delay and signal spread recognized in the distribution are indicative of possible nerve impairment. In another aspect, the Poisson distribution is used to disregard some data as spontaneous activity. For example, this distribution can be used to disregard EMG responses appearing at a far end a lower tail of the Poisson distribution or appearing at a far end of an upper tail of the distribution because there is a very low probability that such responses are truly indicative of the condition of the nerve.

In some embodiments, this distribution tool 114 is used in cooperation with or as part of baseline function 68 of response module 60, as previously described in association with FIG. 1A.

The other functions of tools module 110 generally relates to classifying different features of the measured neurogenic response signals with such functions including but not limited to a correlation function 116, a wavelet function 117, and a Fourier function 118. In general terms, the spreading or narrowing of the EMG response as well as the response amplitude and overall shape of the EMG response is used to identify a damaged or stressed nerve. Further, these methods of classification provided via tools module 110 are used to classify the response waveform into different categories that identify the type and/or extent of the impairment. In one aspect, these methods are used to augment the current methods or employed as a separate method of classifying aspects of the responses to indicate the extent or type of nerve impairment.

In some embodiments, the correlation function 116 is configured to provide auto-correlation and or cross-correlation techniques are used to identify the EMG response waveform as a recognizable stimulated response so that other aspects of a response signal not following such patterns can be ignored. In one aspect, the received data of neurogenic responses is correlated relative to stored response waveforms of different types to classify the response. In one non-limiting example, a first stored response waveform is indicative of compression on a nerve while a second stored response waveform is indicative of excess tension on the nerve. When a waveform in the received data matches one of these respective first or second stored response waveforms, then the correlation function 116 provides an indication of whether the impairment on the nerve is compression or tension. In some embodiments, the neurogenic response waveform is also correlated relative to a baseline response pattern of the target nerve to evaluate changes in the response of the nerve compared to the responses occurring prior to surgery.

In some embodiments, the wavelet function 117 provides another mechanism to classify the response data to recognize patterns indicative of a type or extent of nerve impairment. Likewise in some embodiments, a Fourier analysis is applied via Fourier function 118 to the response data to identify the frequency content of the signals to enhance the identification of changes to the nerve function and/or recognize changes over time. One example of the application of the Fourier function 118 is later described in more detail in association with FIG. 1E and FIG. 1F.

In general terms, the differentiator 112 further sorts the results obtained from tools module 110 to place the measured neurogenic responses into different categories that communicate to the surgeon the type of ongoing trauma to the monitored nerve. In one embodiment, the differentiator 112 includes an irritation parameter 120, a tension parameter 121, a compression parameter 122, a composite parameter 123, or an electrocautery parameter 129.

In some embodiments, differentiator 112 also assists in identifying or differentiating the size of nerve fibers affected by the nerve impairment. For example, the response latency is used to differentiate surgical damage according to the size of the nerve fibers.

In particular, the nerve conduction velocity of the stimulated response propagation is related to the diameter of the axons of the nerve and to the presence or absence, or condition of the myelin sheath. For example, increased nerve conduction velocities are associated with the presence of a myelin sheath and associated with larger nerve axons, resulting in a relatively shorter response latency. In one aspect, damage to the myelin sheath will decrease the conduction velocity, and increase the response latency. In another aspect, by tracking the response latency, one can differentiate the surgical damage relative to the size of the nerve fibers. For example, larger axons will move the signal faster, and thereby produce the shortest latency. Another observable feature includes a larger electromyography response for larger axons which innervates neuromuscular junctions and therefore activates a greater number of motor nerve units.

With this in mind, the irritation parameter 120 identifies a general irritation to the monitored nerve caused by minor tension and is detected by an increase in the response latency and an increase in the evoked response amplitude. The tension parameter 121 identifies impairment by excessive tension and is detected by an increase in response latency and a decrease in the evoked response amplitude. In particular, this excessive tension typically damages the myelin sheath thereby increasing the response latency while the decrease in amplitude is caused by damage to the large axons of the nerve.

The compression parameter 122 identifies impairment by excess compression on the nerve and is detected by a decrease in evoked response amplitude without a substantial change in latency. In particular, this compression is associated with damage to the nerve which results in activation of a decreased number of motor units resulting in the decrease in measured amplitude. Because this compression generally does not significantly affect the myelin sheath over a significant distance, there is no major change in latency.

The composite parameter 123 identifies impairment by more than one type of impairment, such as both compression and tension.

In some embodiments, the electrocautery parameter 129 identifies impairment at least partially caused by an electrocautery event impacting the nerve and is detected via an occurrence of one of the previously described types of nerve impairment simultaneous with or synchronously an electrocautery event or activity during the surgical procedure. For example, electrocautery parameter 129 of differentiator function 112 substantially continuous monitors an RF signal for electrocautery event waveforms via RF input function 69 of monitor 12, as previously described in association with FIG. 1A. When one of the types of impairment (irritation, tension, compression, composite) is separately identified via the measured neurogenic response signals, the electrocautery parameter 129 of differentiator 112 checks to see if the identified impairment occurred synchronously with (at the same time as) an electrocautery event or recognizable electrocautery activity. If so, electrocautery parameter 129 indicates that an electrocautery impairment likely has occurred. This information can guide the surgeon to modify their surgical procedure to avoid any further impact to the nerve during use of the electrocautery device.

Accordingly, in cooperation with the verbal function 98 of notify function 92 (FIG. 1A), differentiator 112 provides a real-time audible indication as a verbal expression to the surgeon of the type of impairment occurring on a monitored nerve, such as an irritation, tension, compression, composite, or electrocautery impairment. Upon hearing such notification, the surgeon can immediately modify or adjust their technique to reduce and/or avoid further impairment to be monitored nerve situated adjacent to their primary surgical target. However, it is understood that other verbal expressions (i.e. words other than irritation, tension, compression, composite, or electrocautery) are selectable or programmable to be audibly communicated to represent the underlying respective general irritation, tension impairment, compression impairment, composite impairment, or electrocautery impairment.

In this way, assessment module 102 and report module 104 of impairment sorter 75 further enable the hands-free and watch-free monitoring of a nerve during surgery.

Figure 1E:
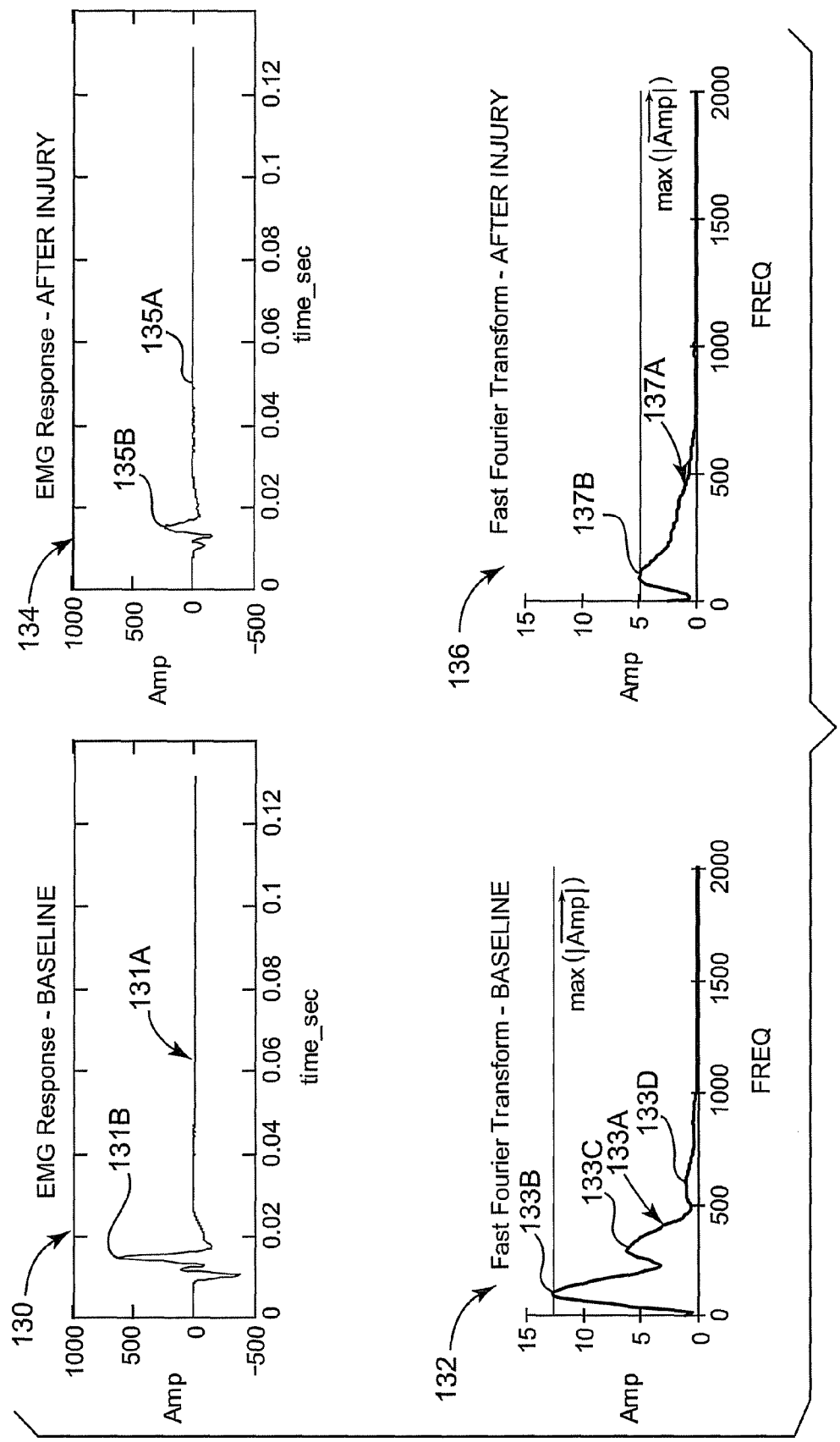
FIGS. 1E and 1F are a series of graphs schematically illustrating a method of evaluating a neurogenic response of innervated muscle, in accordance with principles of the present disclosure.

FIG. 1E provides a series of graphs 130, 132, 134, 136 that schematically illustrate, in both the time domain and the frequency domain, an electromyography (EMG) response as a baseline response pattern and as a response signal after injury of the monitored nerve. In general terms, by applying a fast Fourier transform to this signal information, one can accurately identify the change in the function of the nerve due to impairment while excluding data that is not indicative of this change. With this in mind, graph 130 illustrates a baseline EMG response via signal 131A that has a peak amplitude 131B while graph 132 illustrates a baseline EMG response after application of a Fourier transform. As illustrated in graph 132, the transformed signal 133A includes a first peak 133B, a second peak 133C, and a third peak 133D. The first peak 133B indicates a response amplitude of about 13 while the other peaks 133C, 133D illustrate significantly lower amplitudes in the frequency domain.

As illustrated and described above in association with FIG. 1E, the Fourier transform is applied in a method of identifying one or more signal features of the baseline response pattern (such as, but not limited to, an amplitude) that are indicative of a condition of a nerve. Accordingly, this method includes, at least, comparing the baseline response pattern as expressed in the frequency domain relative to the same baseline response pattern as expressed in the time domain.

In comparison to graph 130, graph 134 illustrates an EMG response after or during impairment to the nerve. As shown in graph 134, response signal 135A includes a peak 135B having an amplitude significantly lower than that shown in graph 134 (i.e., the baseline response of the monitored nerve). However to ensure that an accurate observation is made regarding any changes to condition of the nerve, a Fourier transform is applied to the signal 135A (in graph 134) which results in the signal 137A illustrated in graph 136. By observing the response after or during impairment in the frequency domain provided via graph 136, a single peak 137B corresponding to the response amplitude is clearly recognizable and distinguished from other aspects of the response signal. By comparing the transformed signal 137A in graph 136 and the transformed signal 133A in graph 132, the Fourier function 118 of tools module 110 identifies a significant change in the response amplitude after injury. In particular, graph 132 illustrates a response amplitude of about 13 prior to injury while graph 136 illustrates response amplitude of about 5 after injury. Accordingly, by using the Fourier function 118, a clear indication is provided of the altered condition of the nerve as detected by a change in the response amplitude to a stimulation pulse.

As illustrated and described above in association with FIG. 1E, the Fourier transform is applied to the measured neurogenic response signal in a method of identifying one or more signal features (such as, but not limited to, an amplitude) indicative of a condition of a nerve. Accordingly, this method includes, at least, comparing a measured neurogenic response signal as expressed in the frequency domain relative to the same measured neurogenic response signal as expressed in the time domain.

Figure 1F:
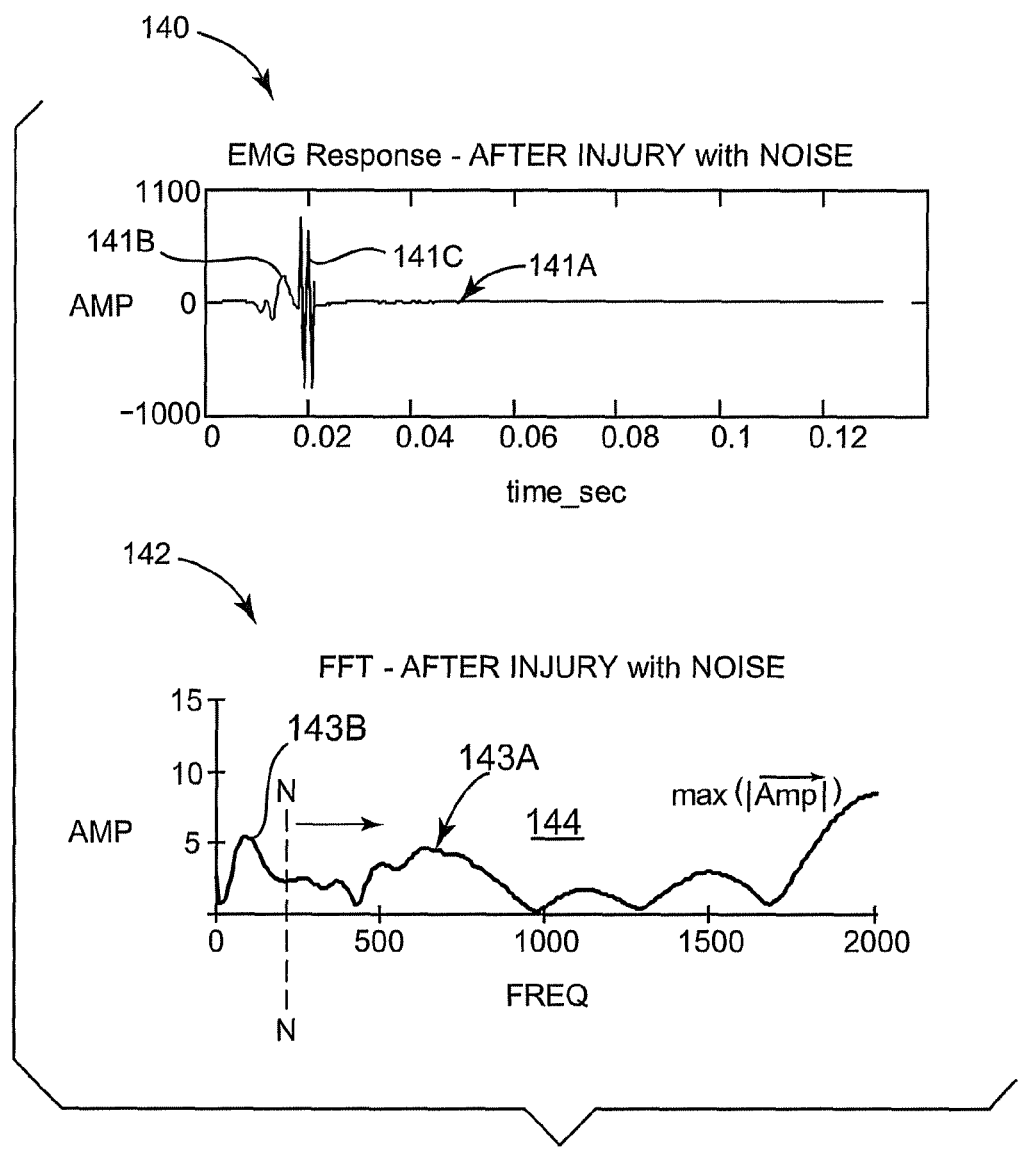

FIG. 1F provides a further schematic illustration of application of Fourier function 118 to an EMG response signal. In particular, FIG. 1F provides graph 140 which illustrates a measured EMG response signal 141A after or during impairment to a nerve where noise is present in the signal. As shown in graph 140, signal 141A illustrates a first response peak 141B and a series of peaks 141C expected to be caused from noise. Meanwhile, graph 142 illustrates a signal 143A that represents the measured EMG response signal 141A of graph 140 after application of a fast Fourier transform via Fourier function 118. As shown in graph 142, the neurogenic response signal is clearly recognizable as peak 143B (based on its similarity to amplitude waveforms of prior neurogenic responses) whereas the noise when expressed in the frequency domain does not match the waveform of a response signal and is excludable from peak 143B. In one aspect, dashed lines N-N represent a demarcation of the response signal waveform (including peak 143B) from the noise appearing to the right of the dashed line and represented by indicator 144.

As illustrated and described in association with FIG. 1F, the Fourier transform is applied to the measured neurogenic response signal in a method of identifying one or more signal features (including, but not limited to, an amplitude) indicative of a condition of a nerve. Accordingly, this method includes analyzing the measured neurogenic response signal in the frequency domain to differentiate noise from the signal features of the measured neurogenic response signal. In one aspect, this differentiation is performed by recognizing the noise as having a pattern in the measured neurogenic response signal in the frequency domain that is substantially different than a pattern of the baseline response pattern in the frequency domain or substantially different than a pattern of one or more prior measured neurogenic response signals (in the frequency domain) without noise.

Accordingly, different classification tools and reporting tools as provided via impairment sorter 75 provide a useful mechanism to sort and evaluate one or more neurogenic responses, which in turn, enhances the ability to detect and classify different types of impairment to a nerve.

FIGS. 2-7 are different views that illustrate a nerve electrode 150, in accordance with principles of the present disclosure that is usable to stimulate a nerve or record a response at a nerve. As illustrated in the perspective views of FIGS. 2 and 3, electrode 150 comprises an elongate body 152 and a cuff portion 160. The nerve electrode 150 includes a proximal end 156 and a distal end 157. In one aspect, the elongate body 152 includes a distal portion 158 adjacent the cuff portion 204 and extends from the distal portion 158 to the proximal end 156 of the electrode 150. In some embodiments, elongate body 152 comprises a ribbed surface 154 and a smooth surface 165 on each of two opposite faces 167 of elongate body 152. In another aspect, elongate body 152 includes opposite side edges 169, which are generally smooth in some embodiments.

Figure 2A:
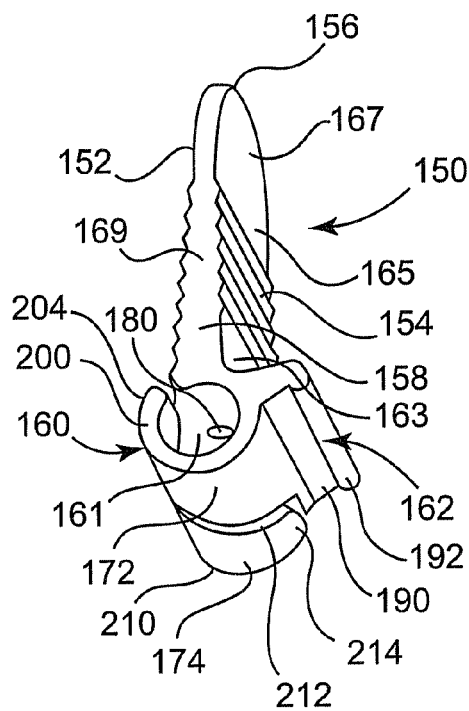
FIG. 2A is perspective view of a nerve electrode, in accordance with principles of the present disclosure.
Figure 2B:
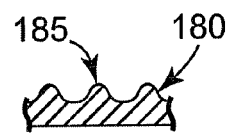
FIG. 2B is a partial sectional view of an electrode contact, in accordance with principles of the present disclosure.
Figure 2C:
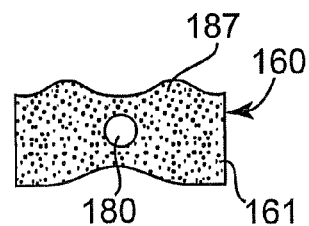
FIG. 2C is a partial plan view of a contact portion of a nerve electrode, in accordance with principles of the present disclosure.
Figure 4:
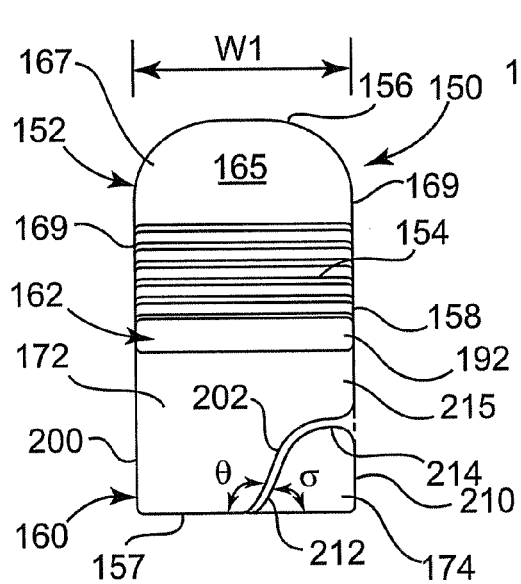
FIG. 4 is front plan view of the nerve electrode of FIG. 2A, in accordance with principles of the present disclosure.
Figure 3:
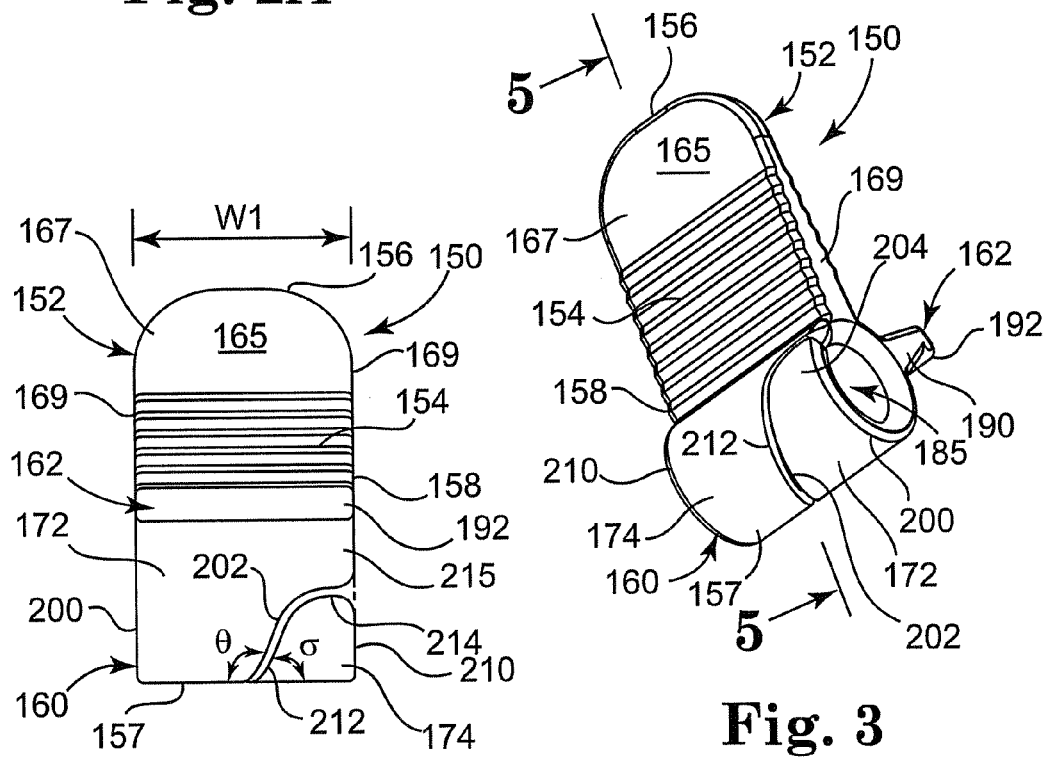
FIG. 3 is another perspective view of the nerve electrode of FIG. 2A, in accordance with principles of the present disclosure.
Figure 5:
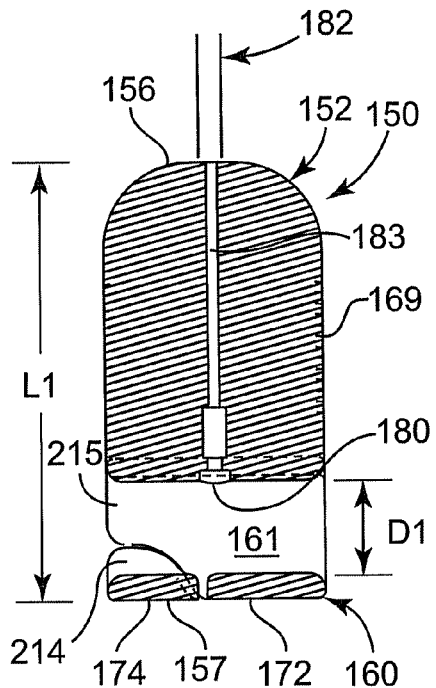
FIG. 5 is sectional view of the nerve electrode as taken along lines 5-5 of FIG. 3, in accordance with principles of the present disclosure.

In further reference to FIGS. 2-4, each respective face 167 has a width (W1 in FIG. 4) substantially greater than an average width (W2 in FIG. 6) of each respective side edges 169. In another aspect, elongate body 152 has a length (L1) substantially greater than an inner diameter (D1) of cuff portion 160, as illustrated in FIG. 5. In one non-limiting example, the length L1 is at least twice as large as, and up to ten times larger than, the inner diameter D1. In another aspect, the width (W1) of face 167 of elongate body 152 (FIG. 5) is substantially greater than the width (W2 in FIG. 6) of side edge 169. In one non-limiting example, the width W1 is at least twice as large as, and up ten times larger than, the width W2.

Accordingly, because the elongate body 152 is substantially longer than a diameter of the cuff portion 160 (and of the lumen 185) and has a substantial width (W1), the elongate body 152 provides a strong support or anchor against which forceps can be used to move tab 162 toward and against the elongate body 152, as further described and illustrated later in association with FIG. 7. In one aspect, the substantial width of the elongate body 152 provides an ample target that the distal tips of the forceps can grasp while the substantial length (L1) of the elongate body provides better reach to facilitate advancing the cuff portion 160 about the nerve 22. With these features in mind, elongate body 152 is sometimes herein referred to as a beam or trunk.

Figure 6:
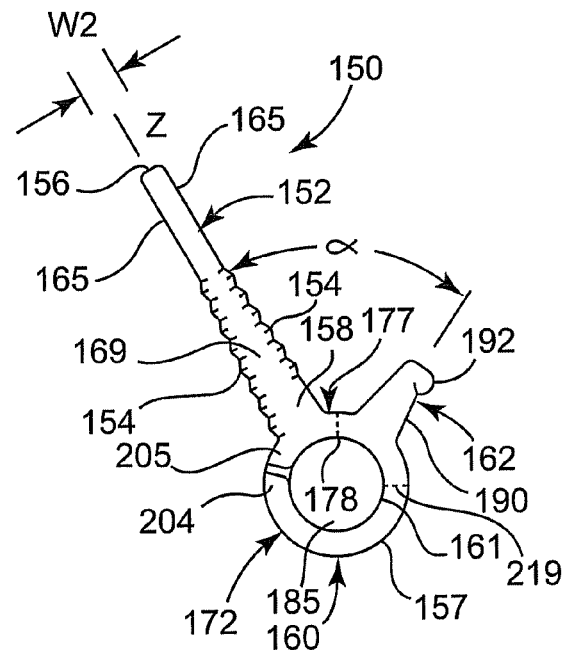
FIG. 6 is a side plan view of the nerve electrode, in accordance with the principles of the present disclosure.

Referring again to FIGS. 2-4, the cuff portion 160 extends distally directly from the distal portion 158 of elongate body 152. In one embodiment, the cuff portion 160 includes a first finger 172 and second finger 174 arranged in a side-by-side relationship (FIGS. 2-5) and extending from a base portion 177. As best seen in FIGS. 5-6, each finger 172, 174 defines a generally arcuate cross-sectional shape. In one aspect, the base portion 177 defines a junction between, and supports both of, the elongate body 152 and tab 162. As further described later, the elongate body 152 and tab 62 also act as a pair of group members of an actuator mechanism while the base portion 177 also functions as a hinge controllable by the actuator mechanism to enable rotational movement of first finger 172 and second finger 174 away from each other, as illustrated in FIG. 7. In particular, the base portion 177 includes a central bending region or central hinge region (represented via dashed lines 178) approximately midway between the trunk 152 and tab 12 such that trunk 152 is off-axis relative to this central hinge region 178. Stated differently, the central hinge region 178 is laterally offset relative to (i.e., not aligned with) a longitudinal axis (represented by line Z as shown in FIG. 6) of trunk 152.

In some embodiments, each finger 172,174 comprises a generally circular cross-sectional shape (best seen in FIGS. 5-6) while in other embodiments, each finger 172,174 comprises a generally elliptical cross-sectional shape. When in their at-rest, closed configuration, the side-by-side combination of the generally circular fingers 172, 174 define lumen 185 which is sized and shaped to receive a nerve. Moreover, because the respective fingers 172, 174 are in this side-by-side relationship along a length of the lumen (i.e., in a direction generally parallel to a longitudinal axis of the nerve that will extend through lumen 185), each finger 172, 174 independently defines at least a portion of a length of the lumen 185.

Moreover, in one aspect, in combination with base hinge portion 177, each respective finger 172, 174 independently provides a substantially 360 degree coverage that encompasses a circumference of the target nerve. In another aspect, in combination with base hinge portion 177, a pair of fingers 172, 174 act together to effectively provide more than 360 degrees (and up to 570 degrees) of coverage that encompass the circumference of the target nerve to the extent that the distal portion of the respective fingers 172, 174 overlap in a side-by-side fashion.

In yet another aspect, the independent 360 degree coverage encompassing the nerve by the separate fingers 172, 174 also provides an automatic mechanism for the nerve electrode 150 to self-adjust its size to different sized nerves while maintaining the electrode contact 180 in direct pressing contact against an outer surface of the nerve. This arrangement contributes to the sealing action of the lumen 185 against an outer surface of the nerve, thereby preventing intrusion of fluids or other matter into the nerve-electrode contact interface, which in turn improves the reliability and quality of the stimulation or recording signal.

In some embodiments, as best seen in FIG. 6, with base portion 177 extending at least from trunk 152 to tab 162, first finger 172 has a radial length generally equal to a radial length of second finger 174 wherein a tip 214 of second finger 174 is represented by dashed line 219. However, it is understood that in other embodiments, the first fingers 172 has a substantially different length than second finger 174.

As best seen in FIGS. 2-4, first finger 172 includes a generally straight outer edge 200 and a generally angled inner edge 202, which converge to form a curved junction at a distal tip 204. Similarly, second finger 174 includes a generally straight outer edge 210 and a generally angled inner edge 212, which converge to form a curved junction at a distal tip 214. In one aspect, as best seen in FIGS. 3-4, the generally angled inner edge 202 of the first finger 172 forms a generally helical relationship relative to the generally angled first edge 212 of the second finger 174. Stated in other terms, the generally angled inner edge 202 of first finger 172 and the generally angled inner edge 212 of second finger 174 form complementary angles relative to each other (as represented by the complementary angles θ and σ illustrated in FIG. 4).

In one aspect, this complementary relationship between the inner edge 202 of the first finger 172 and the inner edge 212 of the second finger 174 enables the first finger 172 and the second finger 174 to be in releasable, slidable contact against each other in a nested arrangement. In one aspect, this nested arrangement enables the angled, side-by-side fingers 172, 174 to provide a more robust enclosure about a nerve than if the inner edges of the fingers were simply generally parallel to each other (along a line generally perpendicular to the lumen or along a line generally parallel to the lumen) or than if the distal ends of the fingers simply contacted each other in a conventional end-to-end closed relationship. In other words, the angled, nested relationship of the fingers 172, 174 results in releasable interlocking of the fingers 172, 174 relative to each other, thereby helping to prevent possible dislodgement of the nerve electrode 150 from becoming dislodged from the nerve about which it is removably secured. Moreover, this releasable interlocking feature of the fingers 172, 174 insures that the electrode contact 180 remains in stable and close fitting contact against the nerve, thereby contributing to accuracy and consistency in applying a stimulation signal to the nerve via the nerve electrode 150.

In another aspect, each finger 172,174 comprises a semi-flexible, generally resilient member. With this construction, the respective fingers 172, 174 generally retain their generally circular or generally arcuate shape in their closed position (shown in FIGS. 2-6) and in their open position shown in FIG. 7. On the other hand, as the fingers 172, 174 move from their closed position to their open position shown in FIG. 7, the base hinge portion 177 (defining a junction between elongate body 152 and tab 162) flexes considerably to permit rotation of the tab 162 toward and against distal portion 158 of elongate body 152. Accordingly, as shown in FIG. 7, the hinge portion 177 generally straightens out to force the distal tips of the respective fingers 172, 174 away from each other. However, as soon as the pressing action of the forceps 194 is removed, tab 162 automatically rotates back to its at-rest position (best seen in FIGS. 2-3 and 5) due to the resiliency of the base hinge portion 177 of cuff portion 160 and thereby allows the return of the fingers 172, 174 to their closed position. In one embodiment, base hinge portion 177 comprises a generally resilient or elastic living hinge, as would be understood by one skilled in the art. With this in mind, beam 152 and tab 162 act as pair of oppositely disposed grip members of an actuator mechanism such that pressing action of the respective grip members activates bending of base hinge portion 177 to cause displacement of fingers 172, 174 away from each other into the open position and release of these grip members reverses bending of base hinge portion 177 to cause fingers 172, 174 to once again releasably engage each other in a side-by-side manner. In some embodiments, in further reference to FIGS. 2-6, first finger 172 includes a substantially larger base portion 215 (adjacent tab 162) than a base portion 205 (FIG. 6) of second finger 174. In one aspect, the large base portion 215 of first finger 172 extending from tab 162 provides a robust support structure to withstand the stress induced when tab 162 is rotated toward elongate body 162 (to move the fingers 172, 174 to their open position) as shown in FIG. 7.

In some embodiments, the body of nerve electrode 150 is formed of a molded elastomeric material suitable to provide the elastic performance of the base hinge portion 177 of electrode 150. In one embodiment, electrode 150 is molded from a rubber material, from a silicone elastomeric material, or other elastomeric material.

In one aspect, as best seen in the sectional view of FIG. 5, electrode lead 182 extends through elongate body 152 with a distal portion of the electrode lead 182 including an electrode contact 180 exposed at surface 161 of cuff portion 160. It is also understood the nerve electrode 150 generally includes lead 182 and that the lead 182 is omitted from FIGS. 2-4 and 6-7 merely for illustrative clarity. Referring again to FIG. 5, a proximal portion of lead 182 extends outwardly from the proximal end 156 of the body 152 for electrical connection to, and electrical communication with, the monitor 12. In one aspect, the electrode contact 180 is a generally circular shaped member of electrically conductive material and is in general alignment with a longitudinal axis of beam 152 and lead 182 extending through beam 152. In one embodiment, the beam 152 and a lead 182 extend and a substantially single direction throughout an entire length of the beam 152.

In some embodiments, the electrode contact 180 includes a generally circular shape defining a first area and the contact portion 161 of the electrode 150 surrounding that the electrode contact 180 defines a second area that is substantially larger than the first area. In combination with the gripping action of the fingers 172,174 (which maintains the electrode contact 180 in pressing contact against an outer surface of the nerve), the substantially larger area of the surrounding contact portion 161 of cuff portion 160 further seals the nerve-to-electrode interface apart from unwanted fluids or other material that could otherwise interfere with the measurement or stimulation on the nerve through the nerve-to-electrode interface.

However, it is understood that in some other embodiments, electrode contact 180 is replaced with an array of spaced apart electrode contact arranged on the contact portion 161 of cuff portion 160 and/or of the fingers 172, 174.

In general terms, the electrode contact 180 of the nerve electrode 150 is configured to enhance a bioelectric contact interface and thereby enhance stimulation and/or recording of neurogenic responses of the target nerve. Accordingly, in some embodiments, the electrode contact 180 comprises a contact material or a contact plating material made from a biocompatible metal (or noble metal) that includes (but is not limited to) one or more of the following materials: 316 Stainless Steel, silver, gold, platinum, palladium, or rubidium. In some embodiments, the contact material or contact plating material of electrode contact 180 is made from a conductive filled flexible circuit, elastomeric material, a conductive ink, or vapor deposited conductor. Moreover, in addition to incorporating a particular type of material, in some embodiments the electrode contact 180 is configured to increase a contact surface area via an irregular surface 185 (such as an undulating surface, a knurled surface, a brushed surface, etc.) as illustrated in FIG. 2B.

In other embodiments, electrode contact 180 is configured to decrease a contact resistance via sintering of the electrode contact or via etching of the contact. As further illustrated in FIG. 2C, drugs are embedded in electrode contact 180 and/or contact portion 161 of nerve-engaging cuff 160 (as represented by markings 186) via mixing or molding the drugs with the respective conductive or elastomeric materials during construction of the electrode contact 180 or contact portion 161. The embedding of drugs enables them to be defused from nerve electrode 150 during surgery or during long term implantation. The embedded drugs include, but are not limited to, anti-inflammatory agents or drugs to promote implant integration and biocompatibility.

In some embodiments, barium sulfate is added to and mixed with the elastomeric material so that the molded nerve electrode 150 forms a visibly radio opaque element viewable under radio fluoroscopy.

In some embodiments, nerve electrode 150 includes the tab 162 forming a protrusion that extends outward from outer portion 168 of cuff portion 160. In one aspect, tab 162 includes a wall portion 190 and a lip 192. In one aspect, the lip 192 extends in direction generally opposite to the elongate body 152 and is configured to reciprocally engage (i.e., releasably catch) a distal tip of a forceps, as further described later in association with FIG. 7. In another aspect, as best seen in side plan view of FIG. 6, tab 162 forms an angle (as represented by α) that is a sub-straight angle (i.e., less than 150 degrees) relative to beam 152. In some embodiments, the angle (α) is between about 30 to about 110 degrees relative to the beam 152. However, in some embodiments, the acute angle is at least about 40 and may extend up to about 90 degrees, while in other embodiments the acute angle is between about 60 to about 70 degrees. In one embodiment, the acute angle between tab 162 and elongate body 152 is about 67 degrees.

Figure 7:
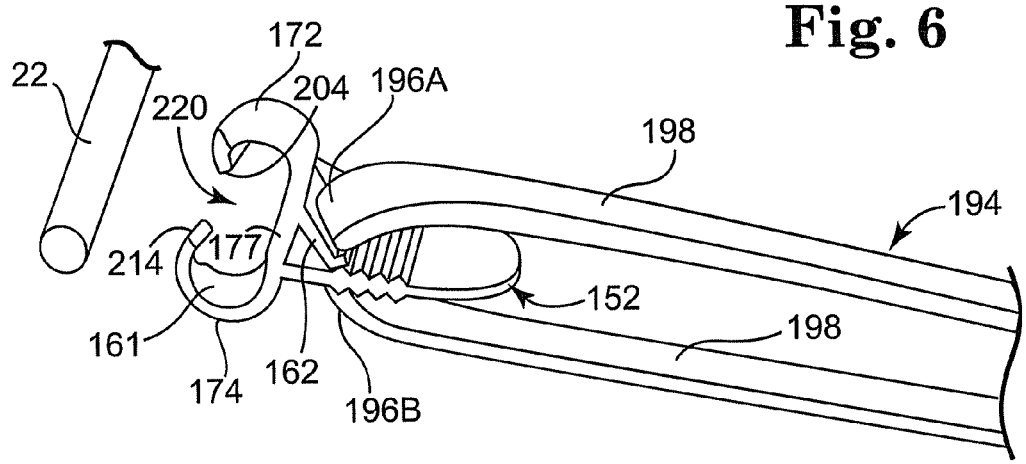
FIG. 7 is a schematic illustration of a method of deploying the nerve electrode, in accordance with principles of the present disclosure.

FIG. 7 is a schematic illustration of a method of installing electrode 150, in accordance with principles of the present disclosure. In this method, a surgeon uses a tool such as a forceps 194 with a squeezing action so that one distal tip 196A of the forceps 194 presses against the tab 162 and engages the lip 192. At the same time, the other distal tip 196B of the forceps 194 presses against the ribbed surface 154 of the elongate body 152. In one aspect, distal tip 196B engages between a pair of ribs of the ribbed surface 154 to prevent slipping of distal tip 196B during the pressing action of the forceps 194. With this pressing action, the user further manipulates the arms 198 of the forceps 194 to squeeze the tab 162 toward the elongate body 152, thereby moving the distal tip 204 of the first finger 172 away from the distal tip 214 of the second finger 174. In other words, pressing action of the tab 162 toward the elongate body 152, results in the bending of the base hinge portion 177 and the formation of an opening 220 between the distal tip 204 of first finger 172 and distal tip 214 of second finger 174.

With the cuff portion 160 in this opened position, the cuff portion 160 is maneuvered about the target nerve 20 until both the contact surface 161 and the electrode contact 180 of the cuff portion 160 engage the target nerve 20, at which time the surgeon releases tab 162 (via opening of distal tips 196 of forceps 194). This action allows the first and second fingers 172, 174 to be released from their open position to their closed position in which first and second fingers 172, 174 resume their side-by-side, releasable interlocking relationship (FIGS. 2-6) that defines lumen 185 encircling the nerve 20.

Figure 8:
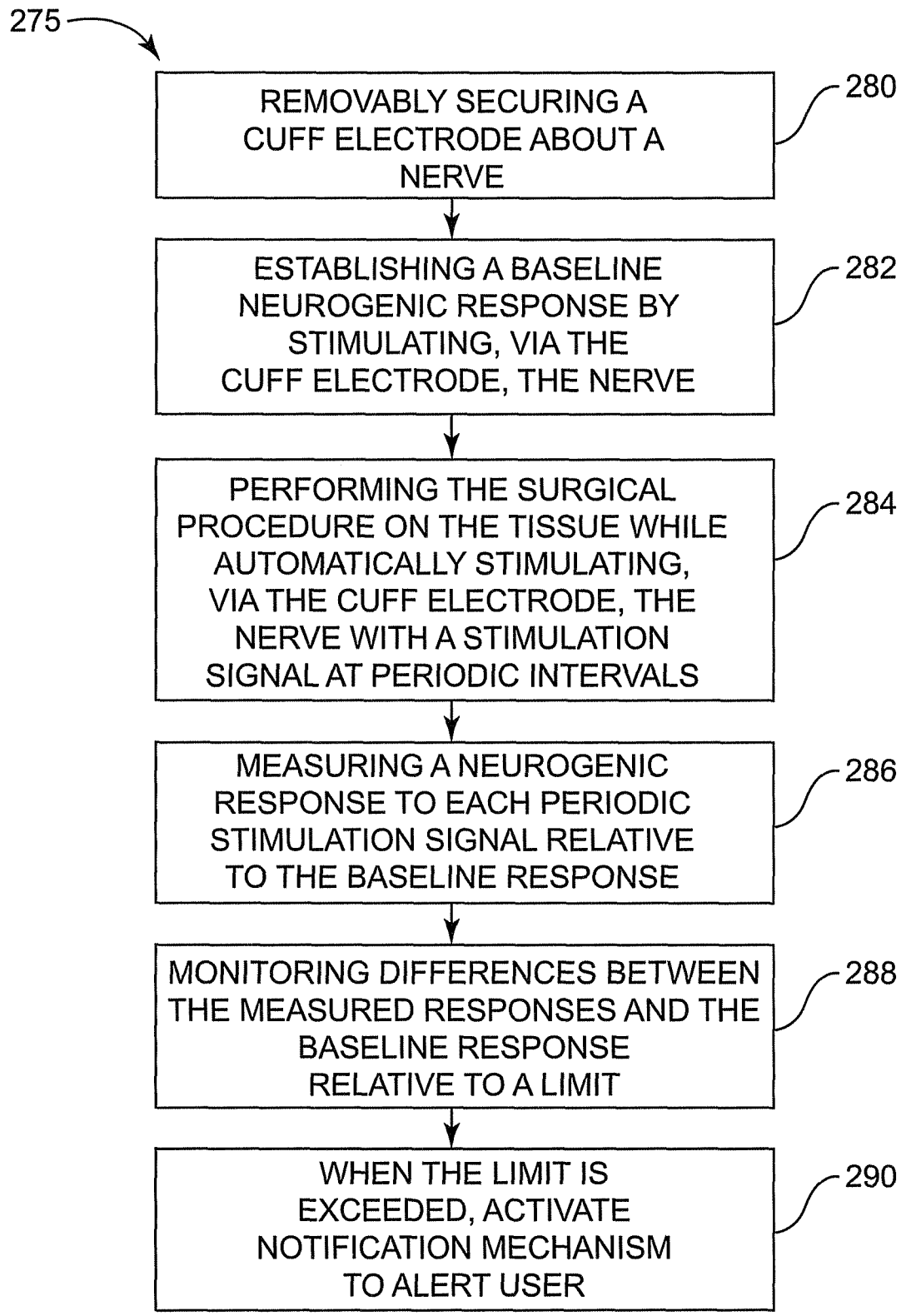
FIG. 8 is a flow diagram of a method of monitoring a nerve, in accordance with principles of the present disclosure.

Keeping in mind the construction of the nerve electrode 150, FIG. 8 illustrates a method 275 of monitoring a nerve during a surgical procedure on a target tissue, in accordance with principles of the present disclosure. In one embodiment, method 275 is performed using a system and/or cuff electrode having at least substantially the same features and attributes as the system 10 and cuff electrodes 20, 150, as previously described in association with FIGS. 1-7. However, in another embodiment, method 275 is performed using systems and/or electrodes other than those described and illustrated in association with FIGS. 1-7.

Referring again to FIG. 8, at 280 method 275 comprises removably securing a cuff electrode about a nerve adjacent to the target tissue and then establishing a baseline neurogenic response pattern of the nerve by stimulating the nerve via the cuff electrode, as shown at 282, in which this neurogenic response is measured at an innervated muscle or directly at the nerve. As shown at 284, the surgical procedure is performed on the target tissue while automatically stimulating (via the cuff electrode) the nerve with a stimulation signal at periodic intervals. The method 275 also includes measuring neurogenic responses to each periodic stimulation signal relative to the baseline neurogenic response pattern (as shown at 286) and then monitoring differences between the measured neurogenic responses and the baseline neurogenic response pattern relative to a limit, as shown at 288. The limit can be a user-defined value, criteria or other threshold. As shown at 290, when the limit is exceeded, the surgeon is then automatically notified (via graphical means or audibly) of any monitored differences or trends of monitored differences that may be indicative of potential impairment to the nerve.

Accordingly, because the cuff electrode is secured about the nerve and the method automatically applies the stimulation signal at periodic intervals, the surgeon can monitor the nerve in a hands-free manner which allows the surgeon to devote more attention to the surgical procedure on the target tissue.

Figure 9:
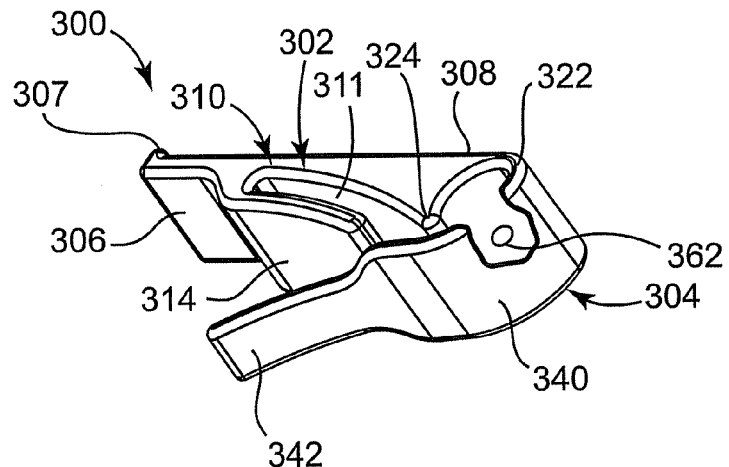
FIG. 9 is a perspective view of a nerve electrode, in accordance with principles of the present disclosure.
Figure 10:
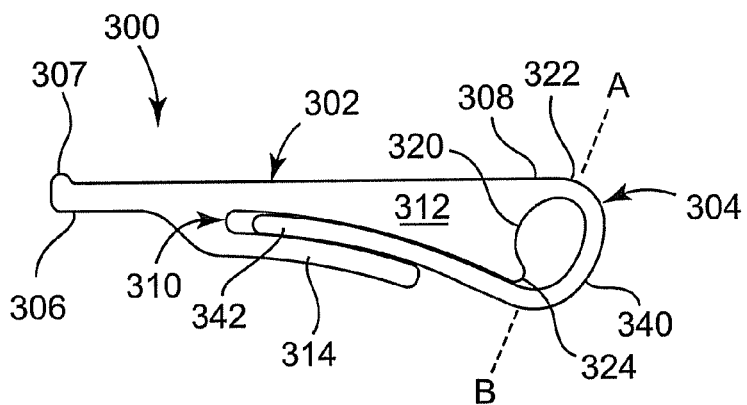
FIG. 10 is a side plan view of a nerve electrode, in accordance with principles of the present disclosure.
Figure 11:
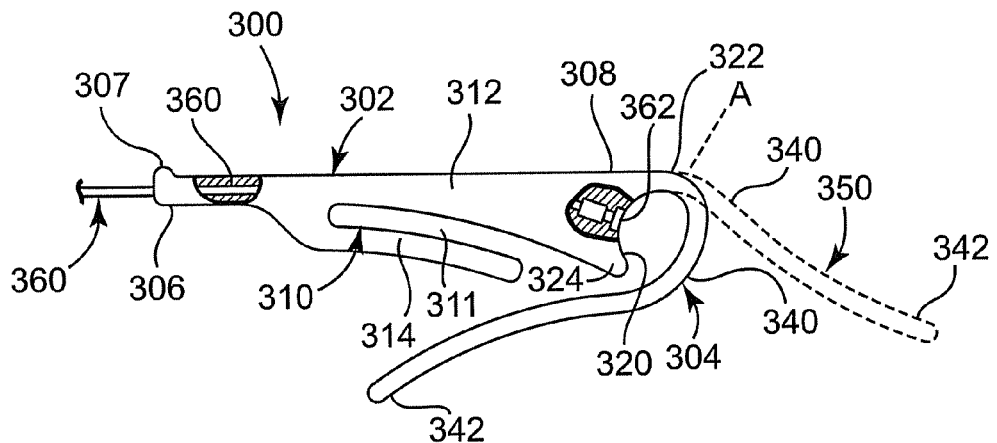
FIG. 11 is partial sectional view of the nerve electrode of FIGS. 9-10, in accordance with principles of the present disclosure.

FIGS. 9-11 are views illustrating a nerve electrode 300, in accordance with the principles of the present disclosure. As illustrated in the perspective view of FIG. 9, nerve electrode 300 comprises an elongate body 302 and a cuff portion 304 extending from the elongate body 302. The elongate body 302 includes a recess 310 and a nerve contact portion 320. The recess 310 is defined by finger 314 and midportion 312 of elongate body 302 while the nerve contact portion 320 includes a first edge 322 and a second edge 324. In one embodiment, as illustrated in FIG. 11, recess 310 includes a mouth 311 oriented in generally the same direction as the generally curved surface of the nerve contact portion 320. In another aspect, as further illustrated in FIG. 11, the recess 310 defines a slot 311 that extends generally parallel to a longitudinal axis of the elongate body 302 and in a direction proximally relative to the nerve contact portion 320.

As further shown in the partial sectional view of FIG. 11, lead 360 extends through the elongate body 302 and includes a contact electrode 362 exposed at a surface of the nerve contact portion 320 of the elongate body 302. In one embodiment, the lead 360 and electrode contact 362 comprises at least substantially the same features and attributes as the lead 182 and electrode contact 180, respectively, previously described in association with FIGS. 2-7.

In general terms, the nerve contact portion 320 forms a generally arcuate shape adapted to wrap around a portion of an outer circumference of the target nerve. In some embodiments, the nerve contact portion 320 forms a generally semicircular shape. In other embodiments, the nerve contact portion 320 forms a generally elliptical shape.

In another aspect, the cuff portion 304 includes a proximal portion 340 and a distal portion 342. The proximal portion 340 extends directly from a first edge 322 (i.e., closed edge) of the nerve contact portion 320 and is bendable relative to the first edge 322 at a point represented by dashed line A in FIG. 11. In one aspect, the cuff portion 304 is formed of a generally flexible and resilient material, so that cuff portion 304 tends to maintain its shape while being adapted to flexibly move between: (1) a generally neutral configuration (FIGS. 9 and 11); (2) an open, insertion configuration (indicated by dashed lines 350 in FIG. 11); (3) and a releasably closed configuration (FIG. 10).

In the neutral configuration shown in FIGS. 9 and 11, distal portion 342 of cuff portion 304 extends freely, independent of the elongate body 302. In this neutral configuration, a surgeon can maneuver the nerve electrode 300 adjacent to a nerve and manipulate the nerve electrode 300 into a removably secured position about the nerve. In particular, the surgeon further manipulates the cuff portion 304 into the open insertion configuration (represented by dashed lines 350 in FIG. 11) and then slidably advances the distal portion 342 of cuff portion 304 underneath the nerve. Upon pulling the distal portion 342 around the nerve, this action brings the nerve contact portion 320 of elongate body 302 into pressing contact against the nerve. Next, using a forceps or other tool, the surgeon removably inserts the distal portion 342 of the cuff portion 304 into recess 310 of elongate body 302 to form the releasably closed configuration of FIG. 10. In the releasably closed configuration, the distal portion 342 of the cuff portion 304 is removably inserted into recess 310, thereby closing proximal portion 340 relative to nerve contact portion 320. This arrangement, in turn, encloses the cuff portion 304 about a nerve to force electrode contact 362 into contact against an outer surface of the nerve. The substantially larger surface area contact portion 320 surrounding electrode contact 362 acts a seal to prevent intrusions of fluids or other matter from interference with the nerve to electrode interface, resulting in their stimulation signals and or recording signals.

With cuff electrode 300 removably secured about the nerve, a surgeon can maintain the integrity of that nerve in accordance with performing method 275 (FIG. 8), in accordance with use of the system 10 and nerve electrode 150 (FIGS. 1-7), or in accordance with other methods or systems adapted to monitor the integrity of a nerve.

Figure 12:
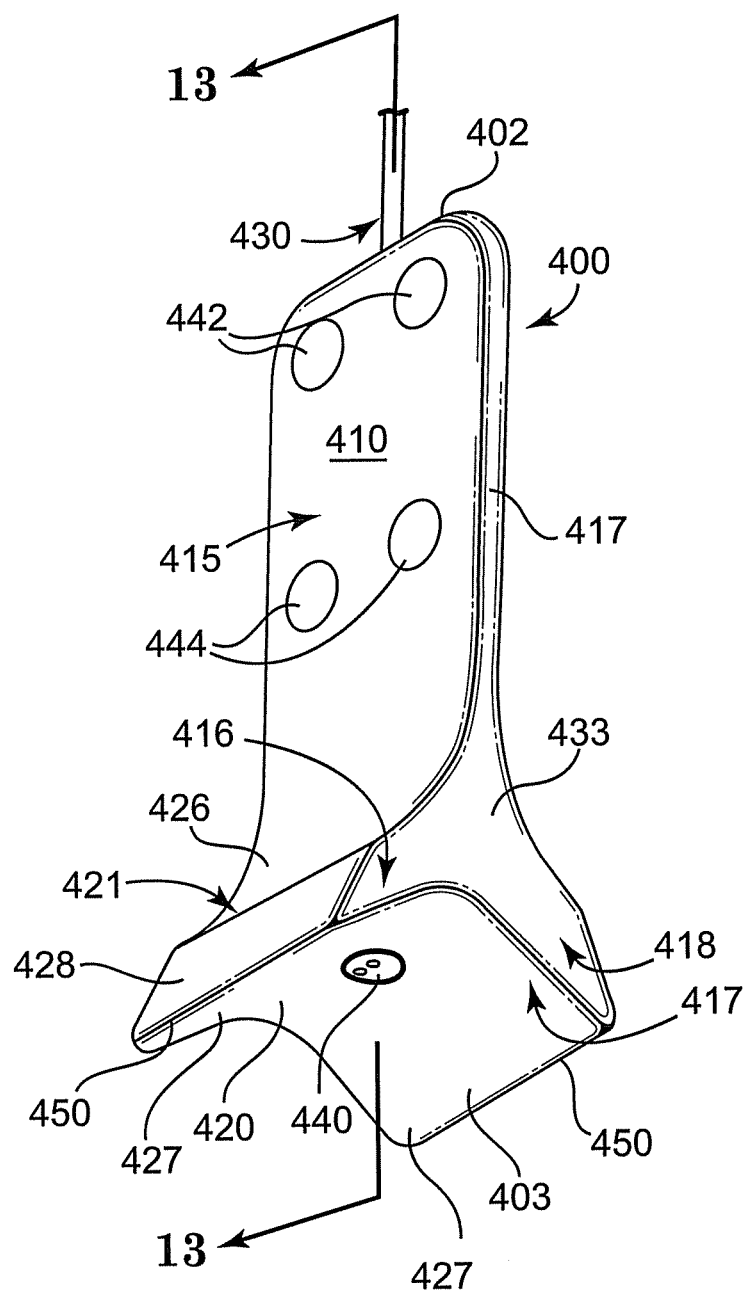
FIG. 12 is a perspective view of a nerve electrode, in accordance with principles of the present disclosure.
Figure 13:
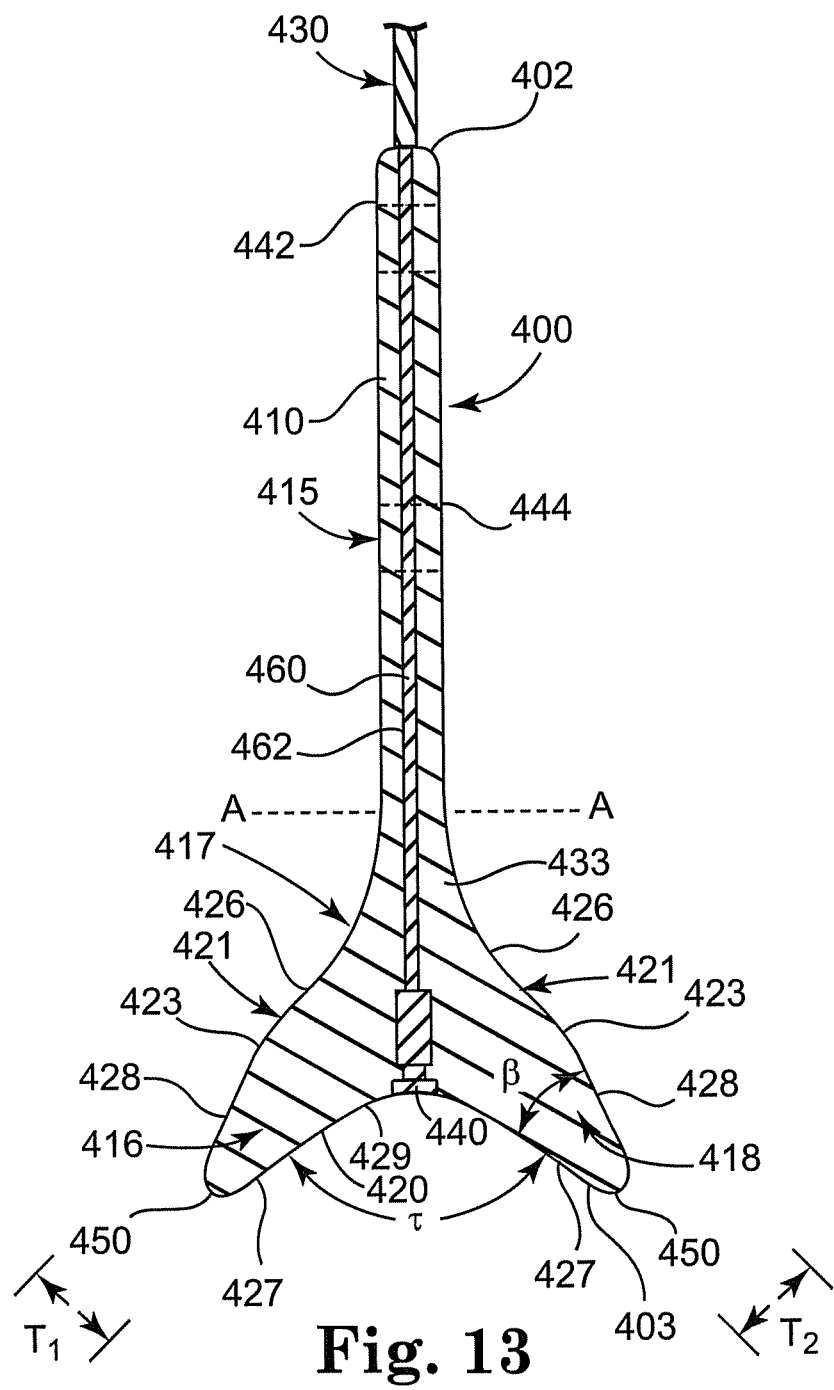
FIG. 13 is a sectional view as taken along lines 13-13 of FIG. 12, in accordance with principles of the present disclosure.
Figure 14:
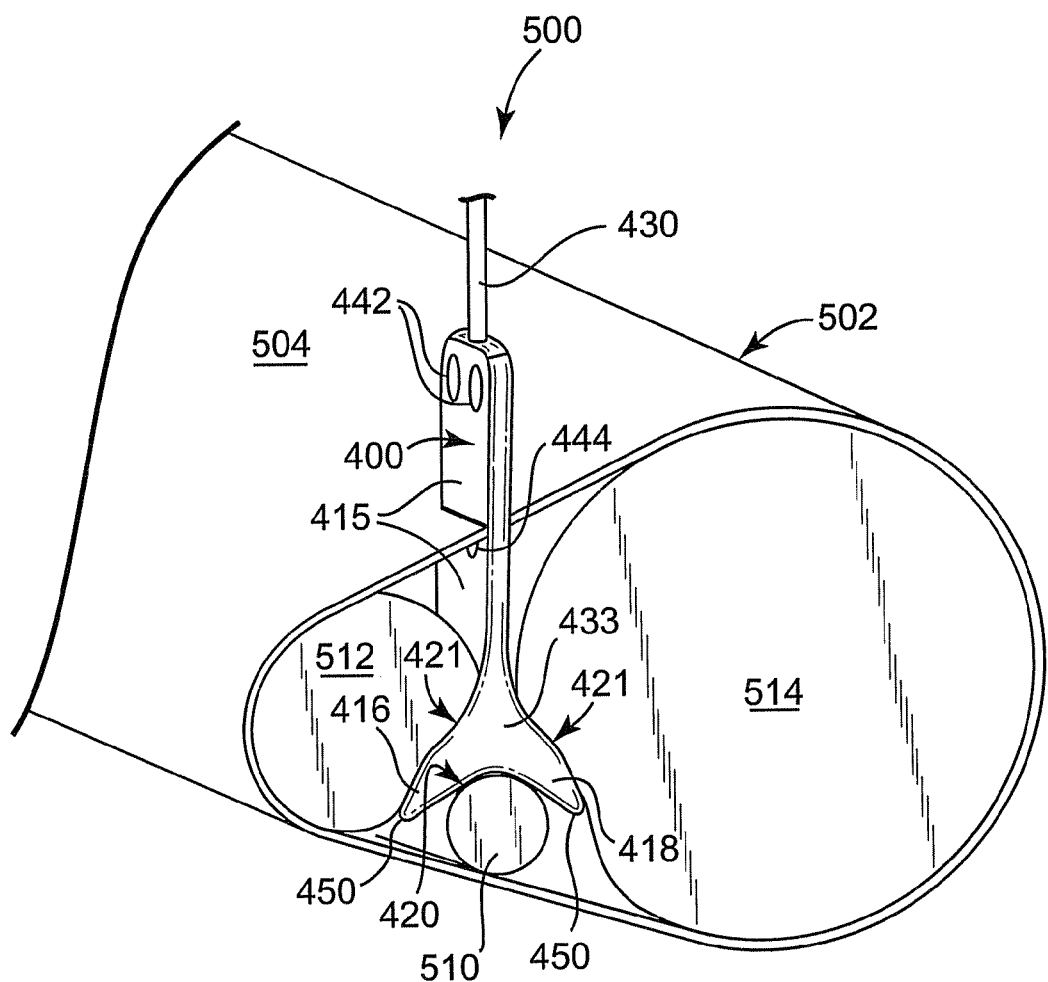
FIG. 14 is a schematic illustration of a nerve electrode releasably engaging nerve within a sheath, in accordance with principles of the present disclosure.

FIGS. 12-14 are views schematically illustrating a nerve electrode 400, in accordance with the principles of the present disclosure. As illustrated in the perspective view of FIG. 12 and the sectional view of FIG. 13, nerve electrode 400 includes a proximal end 402, a distal end 403, a proximal elongate body 415 that forms a trunk, and a distal nerve-engaging portion 417. For illustrative clarity, the transition between the lead body 415 and the distal nerve-engage portion 417 is represented by dashed lines A-A, as shown in FIG. 13.

In general terms, at least a portion of the distal nerve-engaging portion 417 is configured to releasably engage a target nerve to establish electrical communication between an electrode 440 of lead 430 and an outer surface of the respective target nerve. In one embodiment, the target nerve comprises a vagus nerve within a carotid sheath, as will be further described later in association with FIG. 14. In other embodiments, the target nerve comprises a different nerve not located within the carotid sheath.

In one embodiment, the distal nerve-engaging portion 417 forms a generally Y-shaped member as best seen in FIGS. 12-13. In one aspect, the Y-shaped member defines a pair of wedge-shaped fingers or branches 416, 418 that are spaced apart from each other and that form an angle ($\tau$) relative to each other. In one aspect, this arrangement provides a recess portion 420 between the respective fingers 416, 418 wherein the recess portion 420 is configured to slidably engage an outer surface of the target nerve, which in turn, brings an electrode contact 440 into secure engagement in electrical conduction with the outer surface of the target nerve. In one embodiment, recess portion 420 comprises an at least partially concave shape. In one embodiment, this angle ($\tau$) between the fingers 416, 418 is between about 60 and about 120 degrees, while in other embodiments, the angle ($\tau$) is between about 80 and 100 degrees, and in still other embodiments, the angle ($\tau$) is between about 85 and 105 degrees, such as 90 degrees.

In one aspect, electrode 400 further includes electrical lead 430 that extends proximally from the proximal end 402 of elongate body 415. As best seen in FIG. 13, electrical lead 430 also includes a distal portion 460 that extends through a lumen 462 of, and along the length of, the elongate body 415 and the nerve-engaging portion 417. At its distal end, distal portion 460 of electrical lead 430 terminates as the electrode contact 440 exposed at a surface of recess portion 420. In one embodiment, the lead 430 and electrode contact 440 comprises at least substantially the same features and attributes as the lead 182, 360 and electrode contact 180, 362, respectively, as previously described in association with FIGS. 2-7 and 9-11.

In another aspect, as best seen in FIG. 13, each wedge-shaped finger 416, 418 includes an outer side 421 and an inner side 427. In one embodiment, the outer side 421 includes a first portion 426 and a second portion 428 are slightly angled relative to each other and that merge together at peak 423. In some other embodiments, outer side 421 defines a substantially straight portion and that omits peak 423 between first portion 426 and second portion 428.

In some embodiments, the inner side 427 and the second portion 428 of the outer side 421 (of each finger 416, 418) form an angle ($\beta$) of about 30 degrees, and at least falls within a range of about 15 to about 45 degrees. This angle ($\beta$) is selected to achieve the desired amount of anchoring and/or amount of separation between a target nerve and adjacent structures (e.g. nerve, vein, artery, etc.) surrounding the target nerve.

In other embodiments, each finger 416, 418 is configured with a relatively larger angle ($\beta$) that is used to increase the amount of separation between the target nerve and adjacent structures, to increase the degree of anchoring between target nerve and adjacent structure, or to occupy more space created by a relatively smaller sized target nerve or adjacent structure. In one aspect, these larger angles fall within a range between about 25 to 45 degrees. On the other hand, in some embodiments, each finger 416, 418 configured with a relatively smaller angle that is used to decrease the amount of separation between target nerve and adjacent structures, to decrease the degree of anchoring between target nerve and adjacent structures, or to occupy less space created by a relatively larger sized target nerve or adjacent structure. In one aspect, these smaller angles fall within a range between about five and 15 degrees.

In another aspect, the generally Y-shaped member generally corresponds to the general shape of a concave quadrilateral (or concave polygon) in which recess portion 420 of electrode 400 is generally analogous to a concave portion of the concave quadrilateral. In addition, a proximal region 433 of nerve-engaging portion 417 is generally analogous to a convex portion of a concave quadrilateral that is directly opposite the concave portion of the concave quadrilateral. In this arrangement, the two sides of the concave quadrilateral that generally correspond to the inner side 427 of each finger 416, 418 together form the recess portion 420 of electrode 400. Meanwhile, each of the other two sides of the concave quadrilateral generally corresponds to the respective outer side 421 of the respective fingers 416, 418 and are arranged to contact a surrounding tissue on opposite sides of the distal-engaging portion 417. With this arrangement, the general concave quadrilateral shape of the nerve-engaging portion 417 effectively trisects the target nerve and two other adjacent structures. In one aspect, this trisection of the target nerve and surrounding tissues ensures stable and robust anchoring of the nerve-engaging portion 417 relative to the target nerve without encircling the target nerve, thus easing selective release the electrode 400 relative to the target nerve when it is desired to remove the electrode 400 from the target nerve. In one embodiment, both fingers 416, 418 have substantially the same shape and size, while in other embodiments, one of the respective fingers 416, 418 has a size and/or shape that is substantially different (e.g., longer, shorter, wider, narrower, etc.) than the size and/or shape of the other respective finger 416, 418. However, it is understood that in either case, the combination of fingers 416, 418 provide the recess portion 420 configured to engage target nerve 510. In one aspect, the embodiment of differently shaped or sized fingers 416,418 is configured to accentuate separation of target nerve 510 from the other structures within the carotid sheath depending upon the relative size of those other structures and/or the relative spacing between those respective structures and the target nerve 510.

As further illustrated in FIG. 12, elongate body 415 also includes a pair of apertures 442 adjacent proximal end 402 and a second pair of apertures 444 located distal to the first pair of apertures 442. The respective apertures 442 and 444 or sized and positioned on the elongate body 415 and spaced apart from the nerve-engaging portion 417 to facilitate suturing or otherwise fixing elongate body 415 relative to structures surrounding or adjacent to the target nerve.

With this arrangement in mind, FIG. 14 schematically illustrates a method 500 of releasably engaging electrode 400 against a target nerve 510 (e.g., vagus nerve) within a sheath 502 (such as the carotid sheath) and relative to surrounding tissues 512, 514 (such as the internal jugular vein and the common carotid artery). After making an incision in sheath 502, nerve-engaging portion 417 is introduced and advanced within an interior space contained via sheath 502 until the recess portion 420 releasably engages target nerve 510 and until the fingers 416, 418 separate target nerve 510 from each of a first surrounding tissue 512 (e.g., a common carotid artery) and a second surrounding tissue 514 (e.g., an internal jugular vein).

Once the nerve electrode 400 is maneuvered into the position shown in FIG. 14, sutures or other biologically compatible fasteners are used to anchor elongate body 415 of electrode 400. In particular, the first pair of apertures 442 is generally located external to sheath 502 and provide sites for securing sutures or other fasteners onto elongate body 415. These respective sutures or fasteners are then secured to the sheath 502 or other structures. In another aspect, the second pair of apertures 444 is used in a similar fashion to secure the elongate body 415 relative to the sheath 502 and/or other surrounding structures. Accordingly, electrode 400 is robustly, releasably secured for stimulating or monitoring nerve 510 via: (1) the general pressure of tissues within sheath 502 that acts to maintain the nerve-engaging portion 417 in its trisecting position between the target nerve 510 and other tissues 512, 514; and (2) the suturing of elongate body 415 relative to sheath 502 (or other structures) that acts to maintain an orientation of elongate body 415 that further maintains the trisecting position of the nerve-engaging portion 417. Moreover, as seen from FIG. 14, in one embodiment, elongate body 415 has a length configured to ensure that a proximal end 402 (and at least the first pair of apertures 442) extend externally outside of sheath 502 when the nerve-engaging portion 417 is releasably engaging the target nerve 510.

Embodiments of the present disclosure enable consistent and accurate monitoring of the integrity or health of a nerve adjacent to a target tissue during a surgical procedure on that target tissue.

Although the present disclosure has been described with reference to preferred embodiments, workers skilled in the art will recognize that changes can be made in form and detail without departing from the spirit and scope of the present disclosure.

What is claimed is:
1. A nerve monitoring system comprising:
an apparatus including:
a nerve stimulator configured to automatically and periodically apply an electrical stimulation signal to the nerve of a patient's body to elicit an evoked potential, wherein the nerve stimulator is configured to be connected to a nerve stimulation cuff electrode;
a response measurement unit configured to automatically measure, in at least one of a nerve or a muscle of the patient's body, a neurogenic response signal of the evoked potential, the response measurement unit including:
an identification function configured to automatically identify potential nerve impairment based on observable differences between the measured neurogenic response signal and a baseline neurogenic response pattern when the observable differences exceed a threshold, the identification function including an impairment sorter to differentiate multiple, different types of identified potential nerve impairment from each other according to the observable differences, which include at least a relative change in at least a nerve response latency parameter and a nerve response amplitude parameter, and
an alarm configured to automatically audibly announce, upon the identified potential nerve impairment, a verbal expression indicative of the identified type of the potential nerve impairment with a different verbal expression for each of the respective different types of nerve impairment; and
a controller configured to generate control signals, based on executable instructions stored in a memory of the controller, to direct operation of the nerve stimulator and the response measurement unit.
2. The system of claim 1, wherein the measured neurogenic response signal comprises at least one of:
a direct response signal measured at a location of the nerve spaced apart from a location at which the stimulation signal is applied;

an indirect response signal measured at a muscle of the patient's body innervated by the nerve;

a chemical-based neurogenic response signal; or a smooth muscle-based neurogenic response signal.

3. The system of claim 1 wherein, in cooperation with the identification function, the response measurement unit comprises:

a nerve stimulation saturation function to identify an increase or decrease a nerve stimulation saturation of the measured response signal relative to a nerve stimulation saturation parameter of the baseline response pattern.

4. The system of claim 1, comprising:

a nerve stimulation cuff electrode removably securable to the nerve to maintain a continuous electrical pathway from the nerve stimulator of the apparatus to the nerve throughout the surgical procedure; and a response measurement electrode removably securable relative to at least one of the nerve or an innervated muscle to maintain a continuous electrical pathway from the respective nerve or the innervated muscle to the response measurement unit throughout the surgical procedure.

5. The system of claim 1 wherein, in cooperation with the identification function, the response measurement unit comprises:

a nerve stimulation threshold function to identify an increase or decrease a nerve stimulation of the measured response signal relative to a nerve stimulation parameter of the baseline response pattern.

6. The system of claim 1 wherein in the identification function, the identified potential nerve impairment is selected from a group including at least a tension impairment and a compression impairment, and wherein in the alarm, the different verbal expressions include at least a tension impairment-related verbal expression, and a compression impairment-related verbal expression.

7. The system of claim 1 wherein the different verbal expressions include a general impairment-related verbal expression and a composite impairment-related verbal expression.

8. The system of claim 1, wherein the response measurement unit comprises:

a radiofrequency input connectable to an electrically conductive element and configured to detect a potential electrocautery-based nerve impairment via tracking an intensity of radiofrequency signals associated with an electrocautery instrument, and wherein the alarm is configured to automatically audibly announce, upon detection of the potential electrocautery-based nerve impairment occurring substantially synchronous with another respective type of potential nerve impairments, an electrocautery-related verbal expression.

9. The system of claim 8, wherein the electrically conductive element comprises at least one of the electrocautery instrument and a medical lead electrically connectable to a patient body.

10. The system of claim 1, wherein the multiple different types of nerve impairment include a general impairment, a tension impairment, a compression impairment, and a composite impairment.

11. The system of claim 10, wherein the identification function is configured to identify an electrocautery impairment of the nerve as indicated by a detected electrocautery event occurring substantially synchronous with at least one of the types of the minor tension impairment, the tension impairment, the compression impairment, and the composite impairment.

12. The system of claim 10 wherein the general impairment is indicated by an increase in the nerve response latency parameter and an increase in the nerve response amplitude parameter, the tension impairment is indicated by an increase in the nerve response latency parameter and a decrease in the nerve response amplitude parameter, the compression impairment is indicated by a decrease in the nerve response amplitude parameter and a stable response latency, and the composite impairment of the nerve including at least two of the types of the general impairment, the tension impairment, and the compression impairment.

13. The system of claim 12, wherein the general impairment corresponds to the increase in the nerve response latency parameter beyond a first latency limit and the increase in the nerve response amplitude parameter beyond a first amplitude limit, wherein the tension impairment corresponds the increase in the nerve response latency parameter beyond a second latency limit and the decrease in the nerve response amplitude parameter beyond a second amplitude limit, and wherein the compression impairment corresponds to the decrease in the nerve response amplitude parameter beyond the second amplitude limit with the stable response latency.

14. A nerve monitoring system comprising:

an apparatus including:

a nerve stimulator configured to automatically and periodically apply an electrical stimulation signal to the nerve of a patient's body to elicit an evoked potential, wherein the nerve stimulator is configured to be connected to a nerve stimulation cuff electrode;

a response measurement unit configured to automatically measure, in at least one of a nerve or a muscle of the patient's body, a neurogenic response signal of the evoked potential, the response measurement unit including:

an identification function configured to automatically identify potential nerve impairment based on observable differences between the measured neurogenic response signal and a baseline neurogenic response pattern when the observable differences exceed a threshold, and wherein the identification function includes an impairment sorter to differentiate multiple, different types of identified potential nerve impairment from each other according to the observable differences with such differentiation being at least partially determined via:

a nerve refractory recovery parameter of the baseline response pattern, a change in at least one of a double response time, an amplitude, or a latency of a nerve refractory recovery waveform associated with the neurogenic response signal, wherein the nerve refractory recovery waveform is produced in response to a series of the stimulation signals applied according to a paired difference stimulus protocol; and an alarm configured to automatically audibly announce a verbal expression indicative of the identified type of potential nerve impairment with a different verbal expression for each respective different type of nerve impairment; and a controller configured to generate control signals, based on executable instructions stored in a memory of the controller, to direct operation of the nerve stimulator and the response measurement unit.

15. The system of claim 14, wherein the response measurement unit determines the baseline response pattern as an identification of an initial neurogenic status of the nerve according to multiple evoked responses via at least one of:
- a statistical mean of the multiple evoked responses; or
- a variance measurement of the multiple evoked responses.

16. The system of claim 14, wherein the response measurement unit determines the baseline response pattern as an identification of an initial neurogenic status of the nerve via sorting a variability of the multiple evoked responses according to a Poisson distribution.

17. The system of claim 14, wherein the response measurement unit determines the baseline response pattern as an identification of an initial neurogenic status of the nerve according to multiple evoked responses via at least one of:
- an exclusion of a portion of the multiple evoked responses based on a variability of the multiple evoked responses;
- an exclusion of at least one of a maximum value or a minimum value of the multiple evoked responses; or
- an exclusion of non-evoked responses.

18. The system of claim 14, wherein the response measurement unit determines the baseline response pattern as an identification of an initial neurogenic status of the nerve according to multiple evoked responses via at least one of:
- a rate of change of at least one parameter of the multiple evoked responses; or
- a rolling window of multiple evoked responses.

19. The system of claim 14, wherein the first nerve refractory recovery function is configured to apply the series of stimulation signals according to the paired difference stimulation protocol by:
- initially applying a time delay, between a first stimulus pulse and a second stimulus pulse of the pair difference stimulation protocol, that is greater than a natural refractory recovery time period; and
- decreasing the time delay, with each subsequent iterative application of the respective first and second stimulus pulses of the paired difference stimulation protocol, at least until the time delay becomes less than the natural refractory recovery time period.

20. The system of claim 14, wherein the differentiation is at least partially determined via at least a relative change in a nerve response latency parameter and a nerve response amplitude parameter.

21. A nerve monitoring system comprising:
- a response measurement unit configured to automatically measure, in at least one of a nerve or a muscle of a patient's body, a neurogenic response signal of an evoked potential of the nerve in response to electrical stimulation of the nerve, wherein the response measurement unit is configured to be connected to a nerve response electrode and wherein the response measurement unit includes:
  - an identification function configured to automatically identify potential nerve impairment based on differences between the measured neurogenic response signal and a baseline neurogenic response pattern, wherein the potential impairment is identified according to a plurality of different types of potential impairment selected from the group of a general impairment, a tension impairment, a compression impairment, and a composite impairment,
    wherein the identification function includes an impairment sorter configured to differentiate the respective different types of identified impairment via:
    - identification of the general impairment of the nerve as an increase in the latency beyond a first latency limit and an increase in the amplitude beyond a first amplitude limit;
    - identification of the tension impairment on the nerve as an increase in the latency beyond a second latency limit and a decrease in the amplitude beyond a second amplitude limit;
    - identification of the compression impairment on the nerve as a decrease in the amplitude beyond the second amplitude limit with a stable response latency; and
    - identification of the composite impairment on the nerve as both compression and tension on the nerve; and
- an alarm configured to automatically audibly announce, upon the identified potential nerve impairment, a verbal expression indicative of a type of the identified potential impairment with a different verbal expression for each of the respective different types of potential nerve impairment, including at least a tension impairment-related verbal expression, a compression impairment-related verbal expression, and a composite impairment-related verbal expression; and
- a controller configured to generate control signals, based on executable instructions stored in a memory of the controller, to direct operation of the response measurement unit.

22. The system of claim 21 wherein identification function is configured to classify the impairment via application of at least one a correlation process, a wavelet transform, or a Fourier transform to the measured response signal and the baseline response pattern to identify one or more signal features of the measured response signal that substantially differ from the baseline response pattern.

23. The system of claim 22 wherein the identification function is configured to identify, via application of the Fourier transform, one or more signal features of the measured neurogenic response signal and the identification function includes at least one of:
- a differentiation function configured to differentiate, in a frequency domain, a first signal feature in the measured neurogenic response signal from noise in the measured neurogenic response signal; or
- a comparison function configured to compare, in the frequency domain, the first signal feature of the measured neurogenic response signal relative to a corresponding first signal feature in the baseline response pattern.

24. The system of claim 21 wherein the alarm is configured to automatically provide the audible announcement via a communication of the intensity of impairment via at least two different verbal expressions, with each respective verbal expression indicating a different intensity of impairment.

25. The system of claim 21 wherein the audible alarm includes:
- a graduated type of notification in which a volume of the audible announcements are in proportion to a degree of deviation of the measured response from the baseline response pattern.

26. The system of claim 21, wherein the identification function includes:
- a first nerve refractory recovery function configured to identify, relative to a nerve refractory recovery parameter of the baseline response pattern, a change in at least one of a double response time, an amplitude, or a latency of a nerve refractory recovery waveform produced in response to a plurality of the stimulation signals, and wherein the first nerve refractory recovery function is configured to apply the series of stimulation signals according to the paired difference stimulation protocol by:
   initially applying a time delay, between a first stimulus pulse and a second stimulus pulse of the pair difference stimulation protocol, that is greater than a natural refractory recovery time period; and
   decreasing the time delay, with each subsequent iterative application of the respective first and second stimulus pulses of the paired difference stimulation protocol, at least until the time delay becomes less than the natural refractory recovery time period.

27. The system of claim 21, wherein the identification function includes:
   a second nerve refractory recovery function configured to identify, relative to a nerve refractory recovery parameter of the baseline response pattern, a change in at least one of a neurogenic response morphology waveform or a neurogenic response synchrony pattern produced in response to a plurality of the stimulation signals, and
   wherein the second nerve refractory recovery function is configured to apply the series of stimulation signals according to the paired difference stimulation protocol by:
      initially applying a time delay, between a first stimulus pulse and a second stimulus pulse of the pair difference stimulation protocol, that is greater than a natural refractory recovery time period; and
      decreasing the time delay, with each subsequent iterative application of the respective first and second stimulus pulses of the paired difference stimulation protocol, at least until the time delay becomes less than the natural refractory recovery time period.

28. A nerve monitoring system comprising:
   an apparatus including:
      a nerve stimulator configured to automatically and periodically apply an electrical stimulation signal to the nerve of a patient's body to elicit an evoked potential, wherein the nerve stimulator is configured to be connected to a nerve stimulation cuff electrode;
      a response measurement unit configured to automatically measure, in at least one of a nerve or a muscle of the patient's body, a neurogenic response signal of the evoked potential, the response measurement unit including:
         an identification function configured to automatically identify potential nerve impairment based differences between the measured neurogenic response signal and a baseline neurogenic response pattern when the identified differences exceed a threshold, and wherein the identification function includes an impairment sorter to differentiate among a plurality of different types of nerve impairment with such differentiation being at least partially determined according via:
            a second nerve refractory recovery function configured to identify, relative to a nerve refractory recovery parameter of the baseline response pattern, a change in at least one of a neurogenic response morphology waveform or a neurogenic response synchrony pattern produced in response to a series of the stimulation signals applied according to a paired difference stimulus protocol; and
            an alarm configured to automatically audibly announce, upon the identified potential nerve impairment, a verbal expression indicative of each of the different respective types of the identified potential nerve impairment with a different verbal expression for each different respective type of nerve impairment; and
   a controller configured to generate control signals, based on executable instructions stored in a memory of the controller, to direct operation of the nerve stimulator and the response measurement unit.

29. The system of claim 28, wherein the second nerve refractory recovery function is configured to apply the series of stimulation signals according to the paired difference stimulation protocol by:
   initially applying a time delay, between a first stimulus pulse and a second stimulus pulse of the pair difference stimulation protocol, that is greater than a natural refractory recovery time period; and
   decreasing the time delay, with each subsequent iterative application of the respective first and second stimulus pulses of the paired difference stimulation protocol, at least until the time delay becomes less than the natural refractory recovery time period.

30. The system of claim 28, wherein the differentiation is at least partially determined via at least a relative change in a nerve response latency parameter and a nerve response amplitude parameter.

31. A nerve monitoring system comprising:
   a response measurement unit configured to automatically measure, at least one of a nerve or a muscle of a patient's body, a neurogenic response signal of an evoked potential of the nerve in response to electrical stimulation of the nerve, wherein the response measurement unit is configured to be connected to a nerve response electrode and wherein the response measurement unit includes:
      an identification function configured to automatically identify first potential nerve impairment based on differences between the measured neurogenic response signal and a baseline neurogenic response pattern, wherein the first potential nerve impairment is identified according to a plurality of different types of first potential nerve impairments selected from the group of a general impairment, a tension impairment, a compression impairment, and a composite impairment;
      a radiofrequency input connectable to an electrically conductive element and configured to detect a potential electrocautery-based nerve impairment via tracking an intensity of radiofrequency signals associated with an electrocautery instrument; and
      an alarm configured to automatically audibly announce, upon the identified first potential nerve impairment, a verbal expression indicative of a type of the identified first potential nerve impairment with a different verbal expression for each of the respective different types of first potential nerve impairment, including at least a tension impairment-related verbal expression, a compression impairment-related verbal expression, and a composite impairment-related verbal expression; and
   a controller configured to generate control signals, based on executable instructions stored in a memory of the controller, to direct operation of the response measurement unit,
   wherein the alarm is configured to automatically audibly announce, upon detection of the potential electrocautery-based nerve impairment occurring substantially synchronous with a respective one of the first potential nerve impairments, an electrocautery-related verbal expression.

32. A nerve monitoring system comprising:
an apparatus including:
- a nerve stimulator configured to automatically and periodically apply an electrical stimulation signal to the nerve of a patient's body to elicit an evoked potential, wherein the nerve stimulator is configured to be connected to a nerve stimulation cuff electrode;
- a response measurement unit configured to automatically measure, in at least one of a nerve or a muscle of the patient's body, a neurogenic response signal of the evoked potential, the response measurement unit including:
  - an identification function configured to automatically identify potential nerve impairment based on differences between the measured neurogenic response signal and a baseline neurogenic response pattern, wherein the identification function includes a nerve refractory recovery function configured to identify, relative to a nerve refractory recovery parameter of the baseline response pattern, a change in at least one of a neurogenic response morphology waveform or a neurogenic response synchrony pattern produced in response to a plurality of the stimulation signals applied according to a paired difference stimulation protocol;
- a radiofrequency input connectable to an electrically conductive element and configured to detect a potential electrocautery-based nerve impairment via tracking an intensity of radiofrequency signals associated with an electrocautery instrument; and
- an alarm configured to automatically audibly announce, upon identification of a potential nerve impairment, a verbal expression indicative of a type of the identified potential nerve impairment with a different verbal expression for each different type of a plurality of types of nerve impairment; and
- a controller configured to generate control signals, based on executable instructions stored in a memory of the controller, to direct operation of the nerve stimulator and the response measurement unit,
wherein the alarm is configured to automatically audibly announce, upon detection of the potential electrocautery-based nerve impairment occurring substantially synchronous with a respective one of the first potential nerve impairments, an electrocautery-related verbal expression.

33. The system of claim 32 wherein the response module includes:
- an impairment sorter module configured to differentiate the respective different types of impairment as at least one of a general impairment, a tension impairment, a compression impairment, a composite impairment, and an electrocautery impairment and wherein the different verbal expressions audibly announced via the alarm include at least one of the following terms general, tension, compression, and composite,
wherein the impairment sorter module is configured to differentiate the respective different types of identified impairment via at least one of:
  - identification of the general impairment of the nerve as an increase in the latency beyond a first latency limit and an increase in the amplitude beyond a first amplitude limit;
  - identification of the tension impairment on the nerve as an increase in the latency beyond a second latency limit and a decrease in the amplitude beyond a second amplitude limit;
  - identification of the compression impairment on the nerve as a decrease in the amplitude beyond the second amplitude limit and without a change in response latency; and
  - identification of the composite impairment on the nerve as both compression and tension on the nerve.

34. A nerve monitoring system comprising:
a response measurement unit configured to automatically measure, in at least one of a nerve or a muscle of a patient's body, a neurogenic response signal of an evoked potential of the nerve in response to electrical stimulation of the nerve, wherein the response measurement unit is configured to be connected to a nerve response electrode and wherein the response measurement unit includes:
- an identification function configured to automatically identify a first potential nerve impairment based on the measured neurogenic response signal according to a plurality of different types of potential impairment selected from a group including at least a general impairment, a tension impairment, a compression impairment, and a composite impairment;
- a radiofrequency input connectable to an electrically conductive element and configured to detect a potential electrocautery-based nerve impairment via tracking an intensity of radiofrequency signals associated with an electrocautery instrument; and
- an alarm configured to automatically audibly announce, upon detection of the potential electrocautery-based nerve impairment occurring substantially synchronous with a respective one of the first potential nerve impairments, at least an electrocautery-related verbal expression; and
- a controller configured to generate control signals, based on executable instructions stored in a memory of the controller, to direct operation of the response measurement unit.

35. The system of claim 34, wherein the electrically conductive element comprises at least one of the electrocautery instrument and a medical lead electrically connectable to a patient body.

36. The system of claim 1 wherein, in cooperation with the identification function, the response measurement unit comprises at least one of:
- an amplitude function to identify a decrease in the amplitude of the measured response signal relative to an amplitude parameter of the baseline response pattern;
- a latency function to identify an increase in the latency of the measured response signal relative to a latency parameter of the baseline response pattern; or
- an amplitude-based energy function to identify a decrease in an energy of the measured response signal relative to an energy parameter of the baseline response pattern.

* * * * *